(12) United States Patent
Delaloye et al.

(10) Patent No.: US 10,258,464 B2
(45) Date of Patent: Apr. 16, 2019

(54) TRANSCATHETER STENT-VALVES

(71) Applicant: SYMETIS SA, Ecublens (CH)

(72) Inventors: Stéphane Delaloye, Bülach (CH);
Jacques Essinger, St-Prex (CH);
Jean-Luc Hefti, Cheseaux-Noréaz (CH); Youssef Biadillah, Genève (CH);
Luc Mantanus, Lausanne (CH);
Fabien Lombardi, Prilly (CH)

(73) Assignee: SYMETIS SA, Ecublens (CN)

( * ) Notice: Subject to any disclaimer, the term of this patent is extended or adjusted under 35 U.S.C. 154(b) by 0 days.

(21) Appl. No.: 14/777,503

(22) PCT Filed: Mar. 25, 2013

(86) PCT No.: PCT/EP2013/000893
§ 371 (c)(1),
(2) Date: Sep. 15, 2015

(87) PCT Pub. No.: WO2014/139545
PCT Pub. Date: Sep. 18, 2014

(65) Prior Publication Data
US 2016/0038281 A1 Feb. 11, 2016

Related U.S. Application Data

(63) Continuation of application No. 13/839,357, filed on Mar. 15, 2013, now abandoned.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC .... A61F 2/2403; A61F 2/2412; A61F 2/2418; A61F 2/246; A61F 2/2469;
(Continued)

(56) References Cited

U.S. PATENT DOCUMENTS

| 3,755,823 A | 9/1973 | Hancock |
| 4,106,129 A | 8/1978 | Carpentier et al. |

(Continued)

FOREIGN PATENT DOCUMENTS

| AU | 2006328896 A1 | 6/2007 |
| AU | 2007294199 A1 | 3/2008 |

(Continued)

OTHER PUBLICATIONS

Atkins, Cary W. et al., Risk of Reoperative Valve Replacement for Failed Mitral and Aortic Bioprostheses, The Annals of Thoracic Surgery, vol. 65; pp. 1545-1552, 1998.
(Continued)

*Primary Examiner* — Thomas J Sweet
*Assistant Examiner* — Tiffany Shipmon
(74) *Attorney, Agent, or Firm* — Seager, Tufte & Wickhem LLP.

(57) ABSTRACT

A stent-valve for transcatheter implantation to replace a cardiac valve, the stent valve being compressible to a compressed state for delivery, and expandable to an operative state for implantation, the stent-valve comprising a stent, a plurality of leaflets for defining a prosthetic valve, an inner skirt, an outer skirt, and a paravalve seal for sealing against surrounding tissue. In some embodiments, the paravalve seal comprises material that swells in response to contact with blood. In some embodiments, the seal comprises a flap or pocket that is distensible in response to backpressure and/or paravalve back-flow of blood.

20 Claims, 14 Drawing Sheets

(52) U.S. Cl.
CPC .... *A61F 2/2469* (2013.01); *A61F 2210/0061* (2013.01); *A61F 2220/0075* (2013.01); *A61F 2250/0003* (2013.01); *A61F 2250/0069* (2013.01)

(58) Field of Classification Search
CPC ........ A61F 2210/0061; A61F 2250/003; A61F 2/07; A61F 2002/075
See application file for complete search history.

(56) References Cited

U.S. PATENT DOCUMENTS

| | | |
|---|---|---|
| 4,470,157 A | 9/1984 | Love |
| 5,078,720 A | 1/1992 | Burton et al. |
| 5,163,955 A | 11/1992 | Love et al. |
| 5,192,301 A | 3/1993 | Kamiya et al. |
| 5,344,442 A | 9/1994 | Deac |
| 5,354,330 A | 10/1994 | Hanson et al. |
| 5,411,552 A | 5/1995 | Andersen |
| 5,480,424 A | 1/1996 | Cox |
| 5,499,995 A | 3/1996 | Teirstein et al. |
| 5,500,015 A | 3/1996 | Deac |
| 5,540,712 A | 7/1996 | Kleshinski et al. |
| 5,571,174 A | 11/1996 | Love et al. |
| 5,609,626 A | 3/1997 | Quijano et al. |
| 5,653,749 A | 8/1997 | Love et al. |
| 5,662,703 A | 9/1997 | Yurek et al. |
| 5,713,950 A | 2/1998 | Cox |
| 5,713,951 A | 2/1998 | Garrison et al. |
| 5,718,725 A | 2/1998 | Sterman et al. |
| 5,769,882 A | 6/1998 | Fogarty et al. |
| 5,797,960 A | 8/1998 | Stevens et al. |
| 5,807,327 A | 9/1998 | Green et al. |
| 5,817,126 A | 10/1998 | Imran |
| 5,823,956 A | 10/1998 | Roth et al. |
| 5,824,041 A | 10/1998 | Lenker et al. |
| 5,840,081 A | 11/1998 | Andersen et al. |
| 5,855,600 A | 1/1999 | Alt et al. |
| 5,855,601 A | 1/1999 | Bessler et al. |
| 5,861,028 A | 1/1999 | Angell |
| 5,924,424 A | 7/1999 | Stevens et al. |
| 5,938,697 A | 8/1999 | Killion et al. |
| 5,957,949 A | 9/1999 | Leonhardt et al. |
| 5,976,174 A | 11/1999 | Ruiz |
| 5,980,533 A | 11/1999 | Holman |
| 6,029,671 A | 2/2000 | Stevens et al. |
| 6,083,257 A | 7/2000 | Taylor et al. |
| 6,102,944 A | 8/2000 | Huynh et al. |
| 6,110,201 A | 8/2000 | Quijano et al. |
| 6,168,614 B1 | 1/2001 | Andersen et al. |
| 6,171,335 B1 | 1/2001 | Wheatley et al. |
| 6,183,481 B1 | 2/2001 | Lee et al. |
| 6,196,230 B1 | 3/2001 | Hall et al. |
| 6,214,036 B1 | 4/2001 | Letendre et al. |
| 6,254,564 B1 | 7/2001 | Wilk et al. |
| 6,287,334 B1 | 9/2001 | Moll et al. |
| 6,287,339 B1 | 9/2001 | Vazquez et al. |
| 6,331,189 B1 | 12/2001 | Wolinsky et al. |
| 6,350,278 B1 | 2/2002 | Lenker et al. |
| 6,379,383 B1 | 4/2002 | Palmaz et al. |
| 6,401,720 B1 | 6/2002 | Tue et al. |
| 6,406,493 B1 | 6/2002 | Tu et al. |
| 6,409,759 B1 | 6/2002 | Peredo |
| 6,454,799 B1 | 9/2002 | Schreck |
| 6,458,153 B1 | 10/2002 | Bailey et al. |
| 6,530,952 B2 | 3/2003 | Vesely |
| 6,533,807 B2 | 3/2003 | Wolinsky et al. |
| 6,537,310 B1 | 3/2003 | Palmaz et al. |
| 6,562,069 B2 | 5/2003 | Cai et al. |
| 6,569,196 B1 | 5/2003 | Vesely |
| 6,572,652 B2 | 6/2003 | Shaknovich |
| 6,582,462 B1 | 6/2003 | Andersen et al. |
| 6,589,279 B1 | 7/2003 | Anderson et al. |
| 6,613,079 B1 | 9/2003 | Wolinsky et al. |
| 6,635,085 B1 | 10/2003 | Caffey et al. |
| 6,652,555 B1 | 11/2003 | VanTassel et al. |
| 6,682,558 B2 | 1/2004 | Tu et al. |
| 6,682,559 B2 | 1/2004 | Myers et al. |
| 6,695,865 B2 | 2/2004 | Boyle et al. |
| 6,719,787 B2 | 4/2004 | Cox |
| 6,729,356 B1 | 5/2004 | Baker et al. |
| 6,730,118 B2 | 5/2004 | Spenser et al. |
| 6,733,525 B2 | 5/2004 | Yang et al. |
| 6,736,827 B1 | 5/2004 | McAndrew et al. |
| 6,755,855 B2 | 6/2004 | Yurek et al. |
| 6,767,362 B2 | 7/2004 | Schreck |
| 6,790,229 B1 | 9/2004 | Berreklouw |
| 6,805,711 B2 | 10/2004 | Quijano et al. |
| 6,830,584 B1 | 12/2004 | Seguin |
| 6,830,585 B1 | 12/2004 | Artof et al. |
| 6,830,586 B2 | 12/2004 | Quijano et al. |
| 6,849,085 B2 | 2/2005 | Marton |
| 6,875,231 B2 | 4/2005 | Anduiza et al. |
| 6,893,460 B2 | 5/2005 | Spenser et al. |
| 6,908,481 B2 | 6/2005 | Cribier |
| 6,936,066 B2 | 8/2005 | Palmaz et al. |
| 6,942,682 B2 | 9/2005 | Vrba et al. |
| 7,018,406 B2 | 3/2006 | Seguin et al. |
| 7,025,773 B2 | 4/2006 | Gittings et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,141,064 B2 | 11/2006 | Scott et al. |
| 7,179,290 B2 | 2/2007 | Cao |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,217,287 B2 | 5/2007 | Wilson et al. |
| 7,252,682 B2 | 8/2007 | Seguin |
| 7,276,078 B2 | 10/2007 | Spenser et al. |
| 7,285,130 B2 | 10/2007 | Austin |
| 7,316,712 B2 | 1/2008 | Peredo |
| 7,318,278 B2 | 1/2008 | Zhang et al. |
| 7,320,704 B2 | 1/2008 | Lashinski et al. |
| 7,320,705 B2 | 1/2008 | Quintessenza |
| 7,329,278 B2 | 2/2008 | Seguin et al. |
| 7,329,279 B2 | 2/2008 | Haug et al. |
| 7,331,991 B2 | 2/2008 | Kheradvar et al. |
| 7,331,993 B2 | 2/2008 | White |
| 7,338,484 B2 | 3/2008 | Schoon et al. |
| 7,361,189 B2 | 4/2008 | Case et al. |
| 7,371,258 B2 | 5/2008 | Woo et al. |
| 7,374,571 B2 | 5/2008 | Pease et al. |
| 7,377,938 B2 | 5/2008 | Sarac et al. |
| 7,381,218 B2 | 6/2008 | Schreck |
| 7,381,219 B2 | 6/2008 | Salahieh et al. |
| 7,393,358 B2 | 7/2008 | Malewicz |
| 7,393,360 B2 | 7/2008 | Spenser et al. |
| 7,399,315 B2 | 7/2008 | Iobbi |
| 7,402,171 B2 | 7/2008 | Osborne et al. |
| 7,410,499 B2 | 8/2008 | Bicer |
| 7,416,530 B2 | 8/2008 | Turner et al. |
| 7,422,603 B2 | 9/2008 | Lane |
| 7,431,733 B2 | 10/2008 | Knight |
| 7,435,257 B2 | 10/2008 | Lashinski et al. |
| 7,445,632 B2 | 11/2008 | McGuckin, Jr. et al. |
| 7,455,689 B2 | 11/2008 | Johnson |
| 7,470,284 B2 | 12/2008 | Lambrecht et al. |
| 7,470,285 B2 | 12/2008 | Nugent et al. |
| 7,473,275 B2 | 1/2009 | Marquez |
| 7,481,838 B2 | 1/2009 | Carpentier et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,510,572 B2 | 3/2009 | Gabbay |
| 7,510,575 B2 | 3/2009 | Spenser et al. |
| 7,513,909 B2 | 4/2009 | Lane et al. |
| 7,534,261 B2 * | 5/2009 | Friedman ............... A61F 2/2409 623/2.17 |
| 7,556,646 B2 | 7/2009 | Yang et al. |
| 7,578,828 B2 | 8/2009 | Gittings et al. |
| 7,585,321 B2 | 9/2009 | Cribier |
| 7,591,848 B2 | 9/2009 | Allen |

(56) References Cited

U.S. PATENT DOCUMENTS

| | | |
|---|---|---|
| 7,618,446 B2 | 11/2009 | Andersen et al. |
| 7,625,403 B2 | 12/2009 | Krivoruchko |
| 7,632,296 B2 | 12/2009 | Malewicz |
| 7,682,390 B2 | 3/2010 | Seguin |
| 7,780,726 B2 | 8/2010 | Seguin |
| 7,846,203 B2 | 12/2010 | Cribier |
| 7,846,204 B2 | 12/2010 | Letac et al. |
| 7,896,915 B2 | 3/2011 | Guyenot et al. |
| 7,914,575 B2 | 3/2011 | Guyenot et al. |
| 7,947,075 B2 | 5/2011 | Goetz et al. |
| 7,959,672 B2 * | 6/2011 | Salahieh ............... A61F 2/2418 623/1.24 |
| 8,002,825 B2 | 8/2011 | Letac et al. |
| 8,052,749 B2 | 11/2011 | Salahieh et al. |
| 8,057,540 B2 | 11/2011 | Letac et al. |
| 8,092,518 B2 | 1/2012 | Schreck |
| 8,092,520 B2 | 1/2012 | Quadri |
| 8,403,983 B2 * | 3/2013 | Quadri ................... A61F 2/2412 623/1.24 |
| 8,603,159 B2 | 12/2013 | Seguin et al. |
| 8,628,571 B1 | 1/2014 | Hacohen et al. |
| 9,351,831 B2 * | 5/2016 | Braido ................... A61F 2/2412 |
| 2001/0007956 A1 | 7/2001 | Letac et al. |
| 2001/0039450 A1 | 11/2001 | Pavcnik et al. |
| 2002/0177894 A1 | 11/2002 | Acosta et al. |
| 2003/0023300 A1 | 1/2003 | Bailey et al. |
| 2003/0028213 A1 | 2/2003 | Thill et al. |
| 2003/0042186 A1 | 3/2003 | Boyle |
| 2004/0019374 A1 | 1/2004 | Hojeibane et al. |
| 2004/0044361 A1 | 3/2004 | Frazier et al. |
| 2004/0044400 A1 | 3/2004 | Cheng et al. |
| 2004/0093063 A1 | 5/2004 | Wright et al. |
| 2004/0210304 A1 | 10/2004 | Seguin et al. |
| 2004/0254594 A1 | 12/2004 | Alfaro |
| 2004/0260389 A1 | 12/2004 | Case et al. |
| 2005/0043759 A1 | 2/2005 | Chanduszko |
| 2005/0070794 A1 | 3/2005 | Deal et al. |
| 2005/0113910 A1 | 5/2005 | Paniagua et al. |
| 2005/0137681 A1 | 6/2005 | Shoemaker et al. |
| 2005/0137688 A1 | 6/2005 | Salahieh et al. |
| 2005/0137696 A1 | 6/2005 | Salahieh et al. |
| 2005/0137702 A1 | 6/2005 | Haug et al. |
| 2005/0182483 A1 | 8/2005 | Osborne et al. |
| 2005/0267523 A1 | 12/2005 | Devellian et al. |
| 2005/0283231 A1 | 12/2005 | Haug et al. |
| 2005/0288706 A1 | 12/2005 | Widomski et al. |
| 2006/0004442 A1 | 1/2006 | Spenser et al. |
| 2006/0122692 A1 | 6/2006 | Gilad et al. |
| 2006/0161248 A1 | 7/2006 | Case et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0287717 A1 * | 12/2006 | Rowe ................... A61F 2/2412 623/2.11 |
| 2007/0060998 A1 | 3/2007 | Butterwick et al. |
| 2007/0061002 A1 | 3/2007 | Paul et al. |
| 2007/0073387 A1 | 3/2007 | Forster et al. |
| 2007/0118210 A1 | 5/2007 | Pinchuk |
| 2007/0179600 A1 | 8/2007 | Vardi |
| 2007/0198097 A1 | 8/2007 | Zegdi |
| 2007/0213813 A1 | 9/2007 | Von Segesser et al. |
| 2007/0239265 A1 | 10/2007 | Birdsall |
| 2007/0239269 A1 | 10/2007 | Dolan et al. |
| 2007/0244546 A1 | 10/2007 | Francis |
| 2007/0282436 A1 | 12/2007 | Pinchuk |
| 2008/0071361 A1 | 3/2008 | Tuval et al. |
| 2008/0071362 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0125859 A1 | 5/2008 | Salahieh et al. |
| 2008/0140189 A1 | 6/2008 | Nguyen et al. |
| 2008/0161909 A1 | 7/2008 | Kheradvar et al. |
| 2008/0177381 A1 | 7/2008 | Navia et al. |
| 2008/0195199 A1 | 8/2008 | Kheradvar et al. |
| 2008/0208327 A1 | 8/2008 | Rowe |
| 2008/0228263 A1 | 9/2008 | Ryan |
| 2008/0234814 A1 | 9/2008 | Salahieh et al. |
| 2008/0255660 A1 | 10/2008 | Guyenot et al. |
| 2008/0269878 A1 | 10/2008 | Iobbi |
| 2008/0275550 A1 | 11/2008 | Kheradvar et al. |
| 2009/0005863 A1 | 1/2009 | Goetz et al. |
| 2009/0164006 A1 | 6/2009 | Seguin et al. |
| 2009/0171432 A1 | 7/2009 | Von Segesser et al. |
| 2009/0171447 A1 * | 7/2009 | Von Segesser ........ A61F 2/2418 623/1.24 |
| 2009/0276040 A1 | 11/2009 | Rowe et al. |
| 2009/0287299 A1 | 11/2009 | Tabor et al. |
| 2010/0082094 A1 * | 4/2010 | Quadri ................... A61F 2/2412 623/1.26 |
| 2010/0168839 A1 | 7/2010 | Braido et al. |
| 2011/0040374 A1 | 2/2011 | Goetz et al. |
| 2011/0224780 A1 | 9/2011 | Tabor et al. |
| 2011/0264196 A1 | 10/2011 | Savage et al. |
| 2012/0101571 A1 * | 4/2012 | Thambar ............ A61B 17/0057 623/2.17 |
| 2012/0101572 A1 | 4/2012 | Kovalsky et al. |
| 2012/0116496 A1 | 5/2012 | Chuter et al. |
| 2012/0123529 A1 | 5/2012 | Levi et al. |
| 2012/0172982 A1 | 7/2012 | Stacchino et al. |
| 2012/0303116 A1 | 11/2012 | Gorman et al. |
| 2013/0190861 A1 * | 7/2013 | Chau .................... A61F 2/2418 623/2.18 |
| 2013/0310928 A1 * | 11/2013 | Morriss ................ A61F 2/2418 623/2.12 |
| 2014/0194981 A1 * | 7/2014 | Menk .................... A61F 2/2418 623/2.17 |
| 2014/0350668 A1 * | 11/2014 | Delaloye ............... A61F 2/2418 623/2.17 |
| 2018/0263765 A1 * | 9/2018 | Flaction ................ A61F 2/2412 |

FOREIGN PATENT DOCUMENTS

| | | |
|---|---|---|
| AU | 2009/200985 A1 | 4/2009 |
| CA | 2634358 A1 | 6/2007 |
| CA | 2657839 A1 | 3/2008 |
| CA | 2659690 A1 | 3/2008 |
| DE | 20003874 U1 | 6/2000 |
| DE | 19857887 A1 | 7/2000 |
| DE | 102005003632 A1 | 8/2006 |
| DE | 202007005491 U1 | 7/2007 |
| EP | 0592410 A1 | 11/1991 |
| EP | 0657147 A2 | 6/1995 |
| EP | 0696447 A2 | 2/1996 |
| EP | 0943302 A2 | 9/1999 |
| EP | 1093771 A2 | 4/2001 |
| EP | 1251797 B1 | 8/2001 |
| EP | 1267753 B1 | 10/2001 |
| EP | 1262201 A1 | 12/2002 |
| EP | 1264582 A2 | 12/2002 |
| EP | 1598031 A2 | 11/2005 |
| EP | 1968491 A2 | 6/2007 |
| EP | 2059192 A1 | 3/2008 |
| EP | 2033593 A1 | 3/2009 |
| EP | 2047824 A1 | 4/2009 |
| EP | 2074964 A1 | 7/2009 |
| FR | 2874812 A1 | 3/2006 |
| WO | WO 91/17720 | 11/1991 |
| WO | WO 98/29057 A1 | 7/1998 |
| WO | WO 00/28922 A1 | 5/2000 |
| WO | WO 2000/047139 A1 | 8/2000 |
| WO | WO 00/53122 A1 | 9/2000 |
| WO | WO 01/49213 A2 | 7/2001 |
| WO | WO 01/56505 A1 | 8/2001 |
| WO | WO 01/62189 A1 | 8/2001 |
| WO | WO 01/76510 A2 | 10/2001 |
| WO | WO 02/067782 A2 | 9/2002 |
| WO | WO 02/076349 A1 | 10/2002 |
| WO | WO 03/003949 A2 | 1/2003 |
| WO | WO 03/047468 A1 | 6/2003 |
| WO | WO 03/063729 A2 | 8/2003 |
| WO | WO 2005070343 A1 | 8/2005 |
| WO | WO 2005102015 A2 | 11/2005 |

(56) References Cited

FOREIGN PATENT DOCUMENTS

| | | |
|---|---|---|
| WO | WO 2006/058163 A2 | 6/2006 |
| WO | WO 2006/068944 A2 | 6/2006 |
| WO | WO 2006/076890 A1 | 7/2006 |
| WO | WO 2006/083763 A1 | 8/2006 |
| WO | WO 2006/086135 A2 | 8/2006 |
| WO | WO 2006/086736 A2 | 8/2006 |
| WO | WO 2006/127765 A1 | 11/2006 |
| WO | WO 2007/009117 | 1/2007 |
| WO | WO 2007/071436 A2 | 6/2007 |
| WO | WO 2008/028569 A1 | 3/2008 |
| WO | WO 2008/040555 A2 | 4/2008 |
| WO | WO 2008/070442 A1 | 6/2008 |
| WO | WO 2009/024859 A2 | 2/2009 |
| WO | WO 2009/053497 A1 | 4/2009 |
| WO | WO 2009/091509 A1 | 7/2009 |
| WO | WO 2010/008548 A2 | 1/2010 |
| WO | WO 2010/045238 A2 | 4/2010 |
| WO | WO 2010/045297 A2 | 4/2010 |
| WO | WO 2010/049160 A1 | 5/2010 |
| WO | WO 2010/083558 A1 | 7/2010 |
| WO | WO 2011/051043 A1 | 5/2011 |
| WO | WO 2011/057087 A1 | 5/2011 |
| WO | 2012048035 A2 | 4/2012 |
| WO | WO 2013033791 A1 | 3/2013 |
| WO | 2013086132 A1 | 6/2013 |
| WO | WO 2013134214 A1 | 9/2013 |
| WO | WO 2014072439 A1 | 5/2014 |

OTHER PUBLICATIONS

Australian Examination Report dated Mar. 4, 2010 for Australian Application No. 2009200985.
Dewey, Todd M., "Transapical Aortic Valve Implantation: An Animal Feasibility Study", The Annals of Thoracic Surgery, vol. 82, pp. 110-116. 2006.
European Examination Report dated Aug. 11, 2009 for European Application No. 07818037.9, filed Aug. 23, 2007.
European Search Report dated May 29, 2009 for European Application No. 09154935.2, filed Aug. 23, 2007.
Examination Report dated Feb. 6, 2009 for European Application No. 06841127.1, filed Dec. 22, 2006.
International Preliminary Report on Patentability dated Dec. 6, 2011 for Application No. PCT/EP201 0/057798, filed Jun. 3, 2010.
International Preliminary Report on Patentability dated Feb. 24, 2010 for PCT/IB2008/002180, filed Aug. 21, 2008.
International Preliminary Report on Patentability dated Jun. 24, 2008 for PCT/EP2006/012455, filed Dec. 22, 2006.
International Preliminary Report on Patentability dated Mar. 10, 2009 for PCT/EP2007/007413, filed Aug. 23, 2007.
International Preliminary Report on Patentability dated Mar. 26, 2013 for PCT/EP2011/066677, filed D Sep. 26, 2011.
International Preliminary Report on Patentability dated May 8, 2012 and Written Opinion for Application No. PCT/EP201 0/063306, filed Sep. 10, 2010.
International Preliminary Report on Patentability, dated Sep. 15, 2015, for International Application No. PCT/EP2013/000893.
International Search Report dated Apr. 15, 2009 and Written Opinion for Application No. PCT/IB2008/002180, filed Aug. 21, 2008.
International Search Report dated Apr. 17, 2014 for PCT/EP2013/073318, filed Nov. 8, 2013.
International Search Report dated Feb. 17, 2012 for Application No. PCT/EP2011/066677, filed Sep. 26, 2011.
International Search Report dated Jan. 28, 2008 for Application No. PCT/EP2007/007413, filed Aug. 23, 2007.
International Search Report dated Mar. 25, 2009 and Written Opinion for Application No. PCT/EP2008/064558, filed Oct. 27, 2008.
International Search Report dated Nov. 17, 2010 for Application No. PCT/EP2010/063306, filed Sep. 10, 2010.
International Search Report dated Dec. 9, 2010 for Application No. PCT/EP2010/057798, filed Jun. 3, 2010.
International Search Report dated Sep. 27, 2007 for PCT/EP2006/012455, filed Dec. 22, 2006.
Ma, Liang et al., "Double-crowned valved stents for off-pump mitral valve replacement" European Journal of Cardia-Thoracic Surgery, vol. 28, pp. 194-199, 2005.
Mack, M.J., "Minimally invasive cardiac surgery", Surg. Endosc, vol. 20, pp. S488-S492, 2006.
International Search Report dated Sep. 4, 2014 for PCT/EP2014/055044, filed Mar. 13, 2014.
Pawelec-Wojtalk, et al., "Closure of Left Ventricle Perforation with the Use of Muscular VSD Occluder", European Journal of Cardio-thoracic Surgery, vol. 27, pp. 714-716, 2005.
Walther, Thomas et al., "Transapical approach for sutureless stent-fixed aortic valve implantation: experimental results", European Journal of Cardio-thoracic Surgery, vol. 29, pp. 703-708, 2006.
Weerasinghe, Arjuna et al., "First Redo Heart Valve Replacement: A 10-Year Analysis", Journal of the American Heart Association, vol. 99, pp. 655-658, 1999.

\* cited by examiner

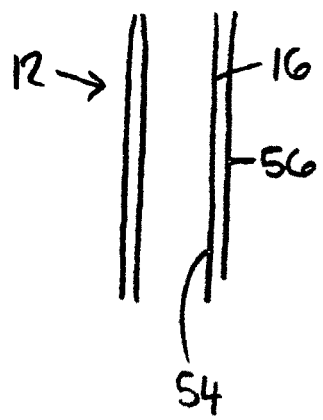
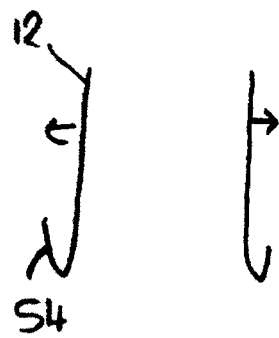
FIG. 5A     FIG. 5B     FIG. 5C
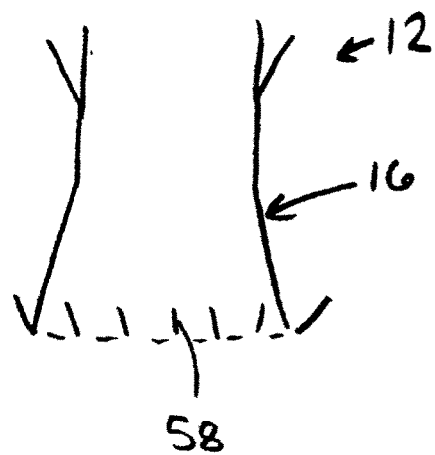
FIG. 6

TRANSCATHETER STENT-VALVES

CROSS REFERENCE TO RELATED APPLICATIONS

This application is a national stage application of and claims priority to International Patent Application No. PCT/EP2013/000893, filed Mar. 25, 2013, and entitled "Improvements Relating to Transcatheter Stent-Valves." This application also claims priority to U.S. patent application Ser. No. 13/839,357, filed Mar. 15, 2013, entitled "Transcatheter Stent-Valves and Methods, Systems and Devices for Addressing Para-Valve Leakage," as well as European patent application no. 12002015.1, filed Mar. 22, 2012. The present application incorporates herein by reference the disclosures of each of the above-referenced applications in their entireties.

FIELD OF THE INVENTION

The present invention relates to the field of transcatheter stent-valves. In some non-limiting aspects, the stent-valve may be a cardiac valve, for example, an aortic valve.

BACKGROUND TO THE INVENTION

Transcatheter valve implantation (for example, transcatheter aortic valve implantation (TAVI)) is an evolving technology for replacement valve therapy that (i) avoids the trauma of conventional open-chest surgery, and (ii) avoids the need for heart and lung bypass. In such a technique, a stent-valve is compressed and loaded into a delivery catheter. The delivery catheter is introduced to the desired site of implantation (for example at the heart) via a percutaneous route or via minimally invasive surgery. The stent-valve is deployed into the implantation position from or by the delivery catheter, and the delivery catheter is then withdrawn.

Despite the successes of transcatheter stent-valves, technological challenges remain. One such challenge is preventing leakage of blood around the stent-valve (so called para-valve leakage). The above stents form a friction fit with the native anatomy to anchor the stent-valve in position, and are round in cross-section. However the native anatomy in which the stent is implanted is often off-round and is different for each person. Moreover, heavy calcification of the native anatomy may obstruct full deployment of any stent, and make the native anatomy even more irregular. It can sometimes be difficult to provide a perfectly sealing fit between the stent-valve and the surrounding anatomy.

In order to address para-valve leakage, it is known to incorporate an external skirt or cover as part of the stent-valve. For example, the skirt is made of compressible biocompatible material, such as paracardial tissue or PET. The thicker the material of the skirt, the more able the skirt is to occlude gaps and effect a seal. However, a disadvantage is that such skirts add to the bulk of the stent-valve. A thick skirt makes the stent-valve problematic to compress to a desirably small size for implantation.

It would be desirable to provide a technique for mitigating para-valve leakage without substantially hindering the compressibility of a stent-valve.

SUMMARY OF THE INVENTION

Aspects of the invention are defined in the claims.

Additionally or alternatively, one aspect of the present invention provides a stent-valve for transcatheter delivery, the stent-valve comprising a stent supporting a plurality of valve leaflets.

Various embodiments present a seal for mitigating para-valve leakage (which may also be referred to herein throughout as a seal or a para(-)valvular seal or a para(-)valvular leakage seal). The seal may be of flexible and/or compliant material. For example, flexible and/or compliant material may comprise natural tissue (e.g. pericardium, such as porcine pericardium or bovine pericardium), and/or synthetic material (e.g. silicone, PET or PEEK, any of which may be in film form, or woven fabric form, or non-woven fabric/mesh form).

In some embodiments, the paravalve seal may be configured to be a substantially supra-annular seal (for example, above the level of a native annulus of the native valve), and/or a substantially annular seal (for example, at the level a native annulus of the native valve), and/or a substantially infra-annular seal (for example, below the level of a native annulus of the native valve).

In some embodiments, a seal is carried by at least one seal support. Additionally or alternatively, a (e.g. deployable) seal support is provided for deploying a seal.

In either case, in some embodiments, the seal support is collapsible to a stowed condition in which the seal is relatively streamlined or compressed with respect to the stent, or to at least a further portion of the stent, when the stent is compressed. (For example, in the stowed condition, the seal support may be generally coplanar with a portion, such as a body portion, of the stent, or may be arranged compressed against the stent or stent portion.) The seal support may be deployable to a deployed condition in which the support holds or biases the seal to a deployed state, for example, with respect to the stent or at least the further portion of the stent previously referred to. The seal support may be self-deploying from the stowed condition to the deployed condition. For example, the seal support may be constrainable in the stowed condition by sheathing of the stent in a compressed state for delivery. The seal support may be self-deploying from the stowed condition when the effect of the constraining sheath is removed. The seal support may be of shape memory material, for example, shape memory metal alloy, for example nitinol.

Various forms and structure of seal support are envisaged. In some embodiments, the seal support, may be integral with the stent (e.g. integrally formed as part of the stent). In other forms, the seal support may be distinct from the stent. Such a seal support may optionally be coupled to or captive on the stent.

The seal support may be configured to bear against the material of the seal without penetrating through the seal material. For example, the seal support may have a shape that distributes contact force. A function of the seal support may be to urge the seal outwardly without the seal support penetrating through the seal material or into a tissue surface against which the seal is desired.

In some embodiments, the seal support comprises a biasing element that biases the seal, for example, to a deployed condition. The seal support (e.g. biasing element) may comprise, for example, a cantilever element (or a plurality of cantilever elements). Each cantilever element may comprise a single strut, or plural struts (for example, first and second struts coupled together at an apex or a tip of the cantilever element). The cantilever elements may be capable of flexing independently of one another, in order to provide a high degree of local seal conformity against an irregular lumen or tissue surface. In some embodiments, each cantilever element is associated with a respective aperture of a lattice structure of the stent. The cantilever elements may, for example, have one end coupled (or integral) with the stent body, and an opposite or remote end that is free to deploy outwardly. The remote end may have a rounded or enlarged or pad tip to avoid having a sharp end that might otherwise risk penetrating through the seal material. The cantilever elements may extend generally in the same direction as each other (e.g. having the remote end directed to one end (such as the outflow end) of the stent-valve), or the cantilever elements may be arranged in two opposite directions (e.g. at least one pointing towards the outflow end, and at least another pointing towards the inflow end), or the cantilever elements may be arranged in a variety of different directions.

In some embodiments, the seal support comprises a ring shape, or tubular shape, or annular member. The member may have an annular coil shape.

In some embodiments, the seal support comprises a member that can be stowed in a generally elongate or helical form, and which deploys to a radially expanded loop form.

In some embodiments, the seal support comprises a portion of the stent that everts from a stowed condition to a deployed condition. Eversion of the stent can provide radial expansion upon deployment without increasing significantly the diameter of the stent when compressed (de-everted). For example, an inflow end or portion of the stent may evert towards the outflow end.

In some embodiments, the stent carries a sealing skirt (or web). The seal support may bias biasing the skirt (or portions thereof) radially outwardly to distend away from the body of the stent.

Additionally or alternatively to the above aspect of the provision of a seal support, a seal of the stent-valve may be configured to be responsive to direction of blood flow past the seal, relative to inflow and outflow ends of the stent-valve. The seal may be configured such that blood flow in a reverse direction (for outflow to inflow) biases the seal to a deployed state to obstruct such flow.

For example, the seal may comprise at least one web defining one or more pockets. The one or more pockets may be configured to fill with blood in response to blood flow in the reverse direction, such that the pocket distends outwardly. Distention of the pocket can fill a gap between the stent-valve and the surrounding anatomy, to obstruct the reverse flow of blood past the pocket.

In some embodiments, the pocket may be defined or carried at a respective aperture of a lattice structure of the stent. The pocket may be defined at least partly by an outer skirt carried on an exterior of the stent. Additionally or alternatively, the pocket may be defined at least partly by an inner skirt carried on an interior of the stent.

Additionally or alternatively to the above aspects, a seal may comprise a skirt at least a portion of which is captive with respect to the stent, and at least a further portion of which is free to deploy or float relative to the stent.

In some embodiments, the further portion may contact a surrounding tissue or lumen wall before the body of the stent is fully deployed. As part of the deployment procedure, the stent may be displaced or biased in a first axial direction to seat against native leaflets. The frictional contact of the skirt against the tissue may cause the further portion of the skirt to bunch or wrinkle in the axial direction during the displacement action. Such bunching or wrinkling may provide additional material to fill voids or gaps between the stent and the surrounding tissue.

Additionally or alternatively, in some embodiments, the further portion of the skirt may be responsive to direction or paravalve blood flow or to pressure of blood acting on the skirt (for example, on the further portion of the skirt). The further portion may, for example, deploy outwardly to contact a surrounding tissue lumen wall. The further portion may form a flap, or generally channel or annular pocket shape in response to, and/or that is responsive to, pressure of blood or flow of blood in the reverse direction. The flap/channel/pocket shape may bias an outer portion of the skirt to seat against the surrounding tissue or lumen surface.

Additionally or alternatively to the above aspects, a seal of the stent-valve may be embossed to present a non-smooth surface. For example, the embossing may be defined by one or more sutures. The one or more sutures may define a zig-zag pattern. The suture may define a generally continuous embossment to obstruct blood flow therepast.

Additionally or alternatively to the above aspects, a seal of the stent-valve may be generally oversized compared to the diameter of the stent. The seal may be bunched or pleated by connections (e.g. suturing) to the stent that causes bunching or pleating between the connections. The bunching/pleating may create additional compliant bulk of seal material able to fill voids or gaps between the stent-valve and the surrounding tissue or lumen surface. The positions of the connections may define bunching or pleating in directions in a pattern that obstructs leakage of blood therepast.

Additionally or alternatively to the above aspects, a seal of the stent-valve may be configured to be self-expanding or self-filling due to a physical property of the seal.

For example, in some embodiments, the seal may be of or comprise a swellable material, foam, sponge or fibrous material. Such a material may self-expand resiliently when the stent deploys. Additionally or alternatively, such a material may absorb blood (and/or a blood component) within its pores or interstices in order to expand the material physically or add bulk.

In some embodiments, the seal may be generally flat and/or tubular in a stowed state and/or may roll or curl into an annular bead or doughnut when in a deployed state. The seal may be self-biased to the deployed state, but be resiliently deformable to the stowed state during compression of the stent for loading into a delivery apparatus. Upon removal of a constraining effect of a sheath of the delivery apparatus, the seal may be configured to readopt the deployed state, in order to provide a radially enlarged seal around the stent.

In some embodiments, at least a portion of the stent comprises a lattice structure, and the stent-valve further comprises one or more seals deployable from or through apertures of the lattice. In one form, the seals comprise web portions of material that define pockets associated with respective apertures of the lattice. The web portions may be configured to distend outwardly from the respective apertures. For example, in some embodiments, the web portions define pockets open on or to one side such that a respective pocket fills with blood to distend outwardly from the aperture of the lattice. Additionally or alternatively, the lattice structure of the stent may comprise biasing elements for biasing the web portions (e.g. pockets) of material radially outwardly from the lattice structure.

In some embodiments, the stent carries a sealing skirt (or web). The stent may comprise biasing elements for biasing the skirt (or portions thereof) radially outwardly to distend away from the body of the stent. The sealing skirt may optionally be carried on the exterior of the stent. An inner skirt (or web) may optionally be carried on the interior of the stent (and optionally coupled directly to the leaflets). At least one of the skirts may be of fabric (e.g. PET). Additionally or alternatively, at least one of the skirts may be of biological tissue, for example, pericardium.

In some embodiments, a biasing element distinct from the stent may bias a seal outwardly. For example, the biasing element may be a ring element (e.g. closed ring or split ring), within an annular seal. The biasing element may be compressible with the stent to a radially compressed condition. The biasing element may expand (e.g. self-expand) towards a radially expanded state when the stent is deployed. The biasing element may be of shape memory material, e.g. nitinol.

Certain features, ideas and advantages of aspects of the invention are identified above and/or in the appended claims, but these do not limit the invention. Protection is claimed for any novel idea or feature described herein and/or illustrated in the drawings whether to not emphasis has been placed thereon.

BRIEF DESCRIPTION OF THE DRAWINGS

Non-limiting embodiments of the invention are illustrated in the accompanying drawings, in which:

FIG. 5a is a schematic view of a seal arrangement in a sheathed non-everted state, FIG. 5b shows initial unsheathing of the seal arrangement of FIG. 5a to permit everting, and FIG. 5c shows the seal arrangement of FIG. 5a when unsheathed.

FIG. 6 is a schematic side view of a further example of seal arrangement with flexible cantilever arms.

DETAILED DESCRIPTION OF EMBODIMENTS OF THE INVENTION

Figure 1:
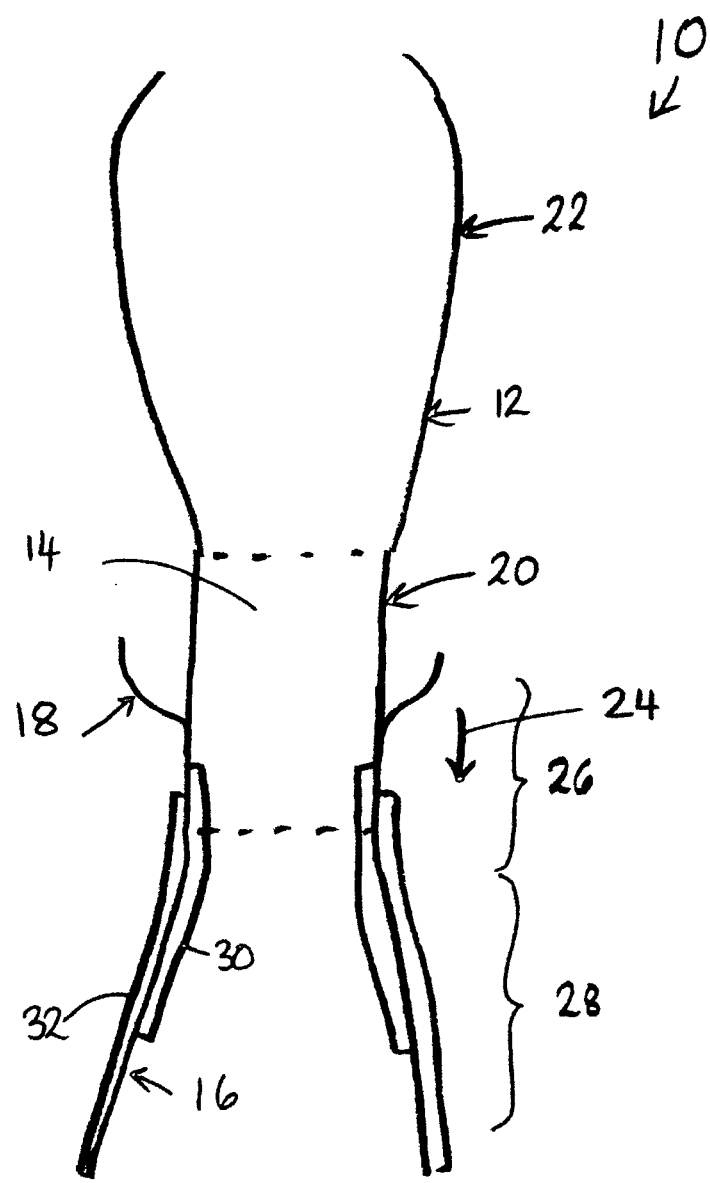
FIG. 1 is a schematic drawing illustrating a stent-valve 10 with which the present invention is suitable to be used.

Referring to FIG. 1 (and FIG. 18), a stent-valve 10 is illustrated for transcatheter implantation. The stent-valve 10 may be a cardiac stent-valve, for example, an aortic stent-valve, a mitral stent-valve, a pulmonary stent-valve or a tricuspid stent-valve, for implantation at the respective valve position in a human heart.

The stent-valve 10 may optionally comprise biological tissue (for example, pericardium (such as porcine pericardium and/or bovine pericardium) and/or natural cardiac valve leaflets (for example, natural porcine cardiac valve leaflets, optionally attached to a portion of natural cardiac wall tissue). The biological tissue may be fixed, for example, using glutaraldehyde. The biological tissue may have anti-calcification properties, for example, having been treated or processed to inhibit or slow calcification (for example, by treatment in alcohol or a process using detergent).

The stent-valve 10 may be compressible to a radially compressed condition (not shown) for delivery using a delivery catheter, and be expandable to an expanded condition (as shown) at implantation. The stent-valve 10 may comprise a stent 12 carrying a plurality of leaflets defining a valve 14. Various geometries of stent 12 may be used. In some embodiments, the stent 12 may include one of more of: a lower tubular or crown portion 16; an upper crown portion 18; a plurality of upstanding commissural supports 20; and a plurality of stabilization arches 22. In use, the lower portion 16 of the stent 12 may be configured to be deployed after the other regions of the stent 12 have first been at least partly deployed. For example, the arches 22, the supports 20 and the upper crown 18 may be deployed at least partly before the lower portion 16 (in that order, or in reverse order, or in a different order). At least once the upper crown 18 has been at least partly deployed, the stent 12 may be urged and/or displaced in the direction of arrow 24 to seat the upper crown 18 against native leaflets at the implantation site. Deploying the lower portion 16 last fixes the stent 12 in its final position.

In some embodiments, at least the lower portion 16, and optionally a portion of the upper crown 18, may be formed by a lattice structure of the stent. The lattice structure may define apertures, for example, generally diamond-shaped apertures.

In some embodiments, the upper crown 18 may be regarded as (e.g., being or comprising) a seal support, when a seal is attached to the upper crown 18. The seal support defined by the upper crown may be considered to deploy the seal at least somewhat outwardly relative to a portion or remainder of the stent just below the upper crown.

The native leaflets may generally overlap a portion 26 of the stent. The native valve annulus may overlap a portion 28 of the stent.

Optionally, the stent-valve 10 may further comprise an inner skirt 30 communicating with the leaflets 14 and carried on an interior of the stent 12. Additionally or alternatively, the stent-valve 10 may further comprise an outer skirt 32 carried on an exterior of the stent 12. When both skirts are provided, the skirts may partially overlap. The skirts may be offset such that one skirt (e.g. the outer skirt 32) extends further towards a lower extremity of the stent 12 than the other (e.g. inner skirt 30). Additionally or alternatively, one skirt (e.g. the inner skirt 30) extends further towards an upper extremity of the stent 12 than the other (e.g. outer skirt 32). The skirts may be of any suitable flexible and/or compliant material, for example, fabric (e.g. of PET), or of plastics film (e.g of PET), or of biological tissue (e.g. of pericardium).

Optionally, at least the outer skirt 32 is positioned to leave (e.g. at least a portion of) the upper crown 18 substantially unobscured by the outer skirt 32. Such an arrangement may assist good blood flow to the coronary arteries (for example, in the case of a stent-valve for the aortic valve).

In some embodiments, the lower portion 16 has an extremity formed with a substantially zig-zag shape. The zig-zag shape may comprise lower apexes 16a and upper apexes 16b. The upper apexes 16b may be masked in FIG. 1 by the superimposed presentation of both the frontmost and rearmost cells of the lattice structure. The zig-zag shape may be substantially continuous around the circumference of the stent 12. The outer skirt 32 may have a peripheral edge having a zig-zag shape that matches substantially the zig-zag shape of the extremity of the lower portion 16. Such an arrangement can avoid excessive material at the extremity, and thereby facilitate crimping of the stent-valve 10. At the same time, the outer skirt 32 covers (for example, completely) open cells of the lattice structure down to the stent extremity to reduce risk of blood leakage through the apertures of the cells. The outer skirt 32 can also provide a layer of material over the struts of the stent, thereby to cushion the engagement between the stent and the sensitive native heart tissue.

The valve 14 may comprise biological tissue, for example, pericardium (such as porcine pericardium or bovine pericardium) or natural cardiac valve leaflets (for example, natural porcine cardiac valve leaflets, optionally attached to a portion of natural cardiac wall tissue). Other biological or non-biological material could also be used for the valve 14, as desired.

The stent 12 may optionally be of a self-expanding type that is compressible to the compressed state for loading into a delivery catheter having a sheath for constraining the stent 12 in the compressed state for delivery to the site of implantation. In use, by removal of the constraining effect of the sheath, the stent 12 self-expands to or (e.g. at least partly) towards the expanded state. A self-expanding stent may, for example, be of shape-memory material, for example, shape-memory metal alloy, for example, nitinol. Additionally or alternatively, the stent 12 may be configured to be expanded by application of an expanding force from the delivery catheter, such as by using an expansion balloon.

There now follows a description of various seal configurations that may be used with the above-described stent-valve 10. The seal configurations may also be used with different stent shapes and configurations. Whether or not described in detail, the following descriptions of seals may use any single or multiple combination of, aforementioned stent and/or stent-valve features.

Suitable materials for a seal may include biological tissue (for example, pericardium, such as porcine pericardium or bovine pericardium). Biological tissue may be fixed tissue, for example, processed using glutaraldehyde. Pericardium is useful because of its very good flexibility, allowing the seal to conform to fit against and around the irregular shape of hard calcifications. Additionally or alternatively, suitable material for a seal may include plastics (for example, PET or PEEK). Plastics may be used in woven or non-woven fabric form, and/or in sheet form and/or film form, as desired. Plastics may combine toughness with suitable flexibility and conformability. The plastics may be of a biocompatible type.

Figure 2A:
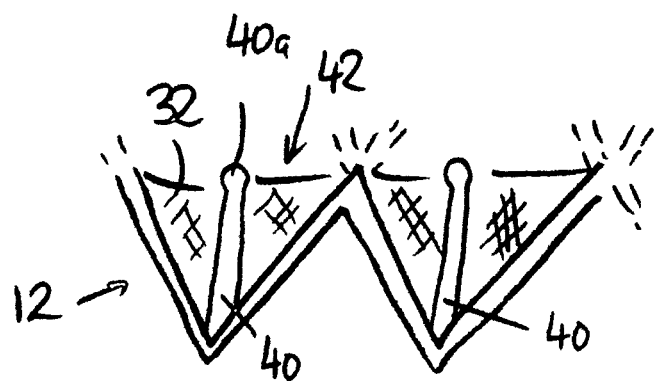
FIG. 2a is a front view of a seal arrangement with cantilevered seal supports.
Figure 2B:
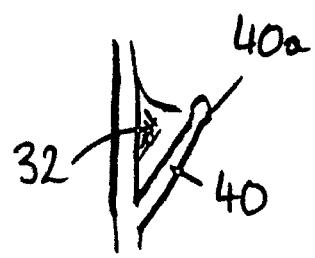
FIG. 2b is a side view of FIG. 2a in a deployed configuration.

FIG. 2 illustrates a first example of seal support in the form of a plurality of cantilever elements 40 mounted on or integral with the stent 12. Each cantilever element 40 may be associated with a respective aperture 42 of the lattice structure. Each cantilever element 40 may be bendable generally independently of the others. Each cantilever element 40 may be movable between a stowed condition, in which the cantilever element is generally coplanar with the portion of the stent 12 around the aperture 42 (or at least is compressed to lie directly or indirectly thereagainst), and a deployed condition in which the cantilever element 40 is biased radially outwardly from the body (e.g. lower portion 16) of the stent 12 (FIG. 2b). The seal support urges a seal (e.g. the outer skirt 32) outwardly so as to fill gaps or voids between the stent-valve 10 and the surrounding lumen/tissue. The ability of the cantilever elements 40 to flex independently can provide a high degree of local conformity. Each cantilever element 40 may have a remote end 40a in the form of a rounded, or pad-like, or other non-damaging shape that can bear against the seal material to bias the seal radially outwardly, without penetrating through, or puncturing, the seal material. In the example shown, each cantilever element 40 may comprise a single strut.

The cantilever elements 40 may be arranged generally in the same orientation (e.g. with the remote ends 40a directed towards one end, e.g. the outlet end, of the stent 12), or distributed to be orientated in two opposite directions, or be distributed to be orientated in a variety of different directions.

The seal urged by the cantilever elements 40 may be generally continuous, or it may be discontinuous in the form of webs or pockets. The pockets may be arranged such that back-pressure of blood, or para-valvular blood flow in the reverse direction from outlet to inlet end of the stent 12, fills the pockets to cause the pockets further to distend, thereby enhancing the seal effect to obstruct such para-valvular flow. Further detail of such pockets is also described with reference to FIG. 13, and any of such features may also be used with the present example. The seal may optionally be attached to the cantilever elements 40, or the seal may be unattached such that the cantilever elements 40 interact with the seal by pushing outwardly.

Figure 3:
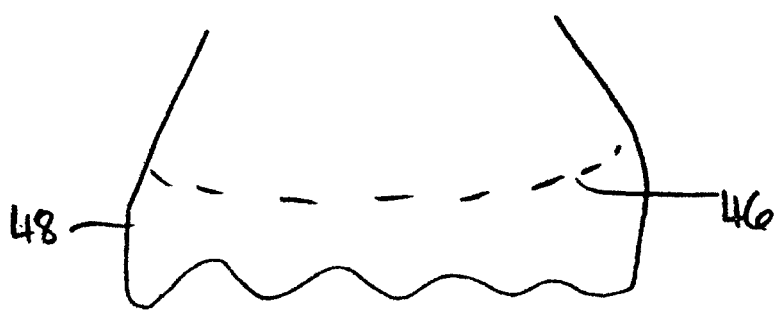
FIG. 3 is a schematic view of a seal arrangement with an annular wire seal support.

Referring to FIG. 3, a seal support 46 is illustrated in the form of an annular wire or ring that is oversize compared to the stent 10. The annular wire is compressible to a stowed state when the stent is compressed, and expands to a deployed state when unconstrained, to urge the seal 48 to a radially expanded state to form a seal against the surrounding tissue/lumen.

Figure 4A:
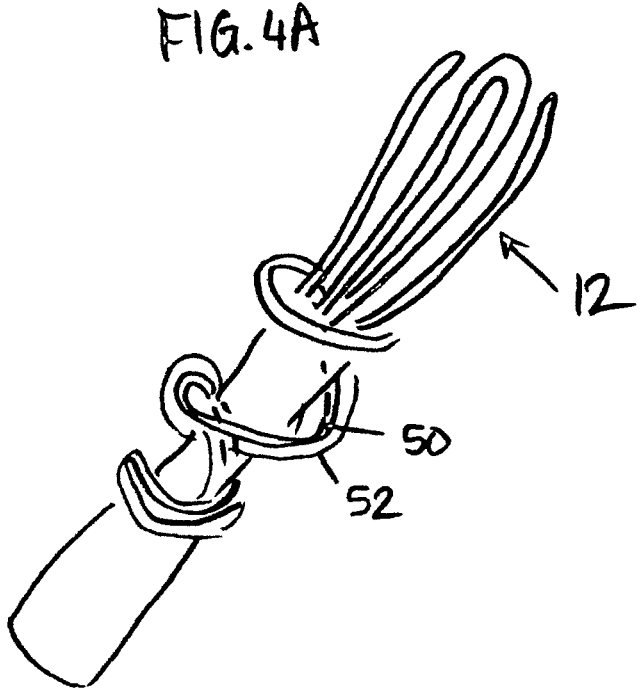
FIG. 4a is a schematic perspective view of an elongate seal support around the stent in a compressed state.
Figure 4B:
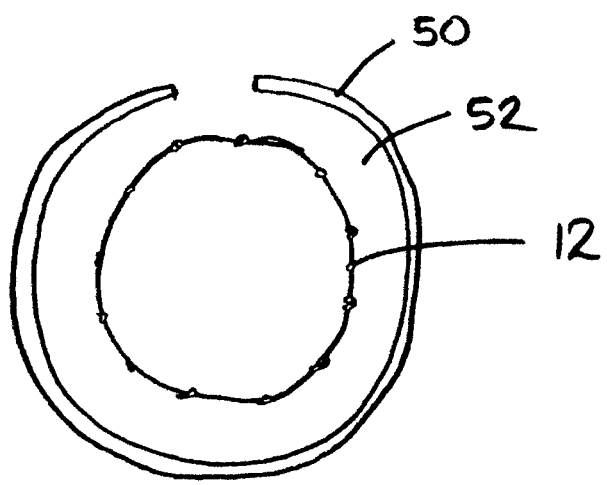
FIG. 4b is a schematic top view of the seal when in a deployed state.

Referring to FIG. 4, a seal support 50 is illustrated in the form of an elongate member carrying a seal 52. The seal support is compressible to a stowed form (FIG. 4a) for example a helical shape around the stent 12 when in its compressed state. The seal support is expandable to a deployed state (FIG. 4b), for example, a radially expanded closed or semi-closed loop form in which the seal support presents the seal 52 in expanded form around the stent 12.

Referring to FIG. 5, a seal support 54 is illustrated in the form of an everting portion of the lower region 16 of the stent 12. The seal support 54 is movable between a stowed, non-everted configuration and a deployed, everted configuration. In a compressed form constrained by a sheath 56 (FIG. 5a), the lower portion of the stent including the seal support 54 is generally tubular (non-everted). As the sheath 56 is progressively removed axially (FIG. 5b), the seal support 56 is unsheathed. Unconstrained, the seal support 56 everts to its deployed state in which the seal is presented and/or biased radially outwardly from the stent body. Further unsheathing of the stent 12 or the lower portion 16(FIG. 5c) permits the stent 12 to expand to its expanded state. The everted seal support 54 urges the seal into tight sealing contact with the surrounding tissue/lumen. The seal may be carried on the inners surface of the stent when compressed, and presented in an outward direction when everted.

FIG. 6 illustrates a seal support that is similar to both FIGS. 2 and 5. The seal support 58 comprises flexible cantilever elements at the lower portion 16 of the stent 12, similar to those of FIG. 2. The seal support 58 also resembles the everted state of the seal support 56 of FIG. 5. In the example of FIG. 6, the cantilever elements do not move between an everted and non-everted state. In the stowed state, the cantilever elements are generally flat against or within the structure of the stent 12 (similar to FIG. 2).

Figures 7A, 7B:
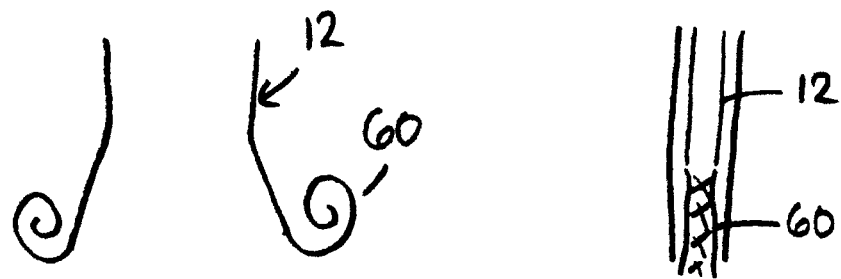
FIG. 7a is a schematic side view of a seal arrangement comprising a rollable cuff when in a deployed state.
FIG. 7b is a schematic view of the seal arrangement when in a stowed, sheathed state.

FIG. 7 illustrates a seal in the form of a rollable bead or cuff 60. The rollable cuff 60 may be self-biased or it may be supported by a seal support frame that tends to roll the cuff 60. In a stowed state (FIG. 7b), the cuff is unrolled to define a generally flat tubular form. The cuff may be constrained in the stowed state by a constraining sheath 62 of a delivery device. When unsheathed, the cuff 60 is free to move to its deployed state (FIG. 7a) in which the cuff 60 rolls up to define a cuff or bead shape. Such a seal provides a compliant bead of material to fill any gap between the stent 12 and the surrounding tissue/lumen.

Figure 8:
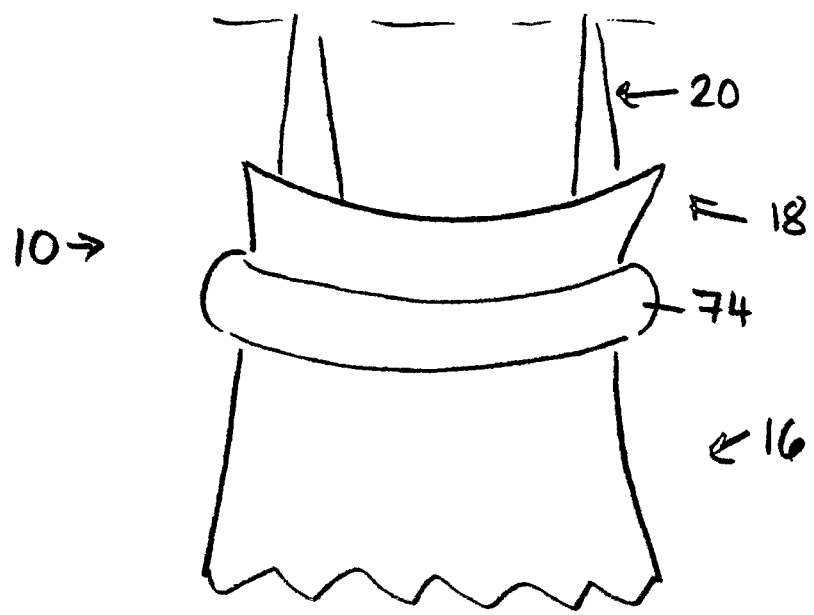
FIG. 8 is a schematic side view of a seal arrangement comprising a porous material.

FIG. 8 illustrates a seal 74 in the form of foam, or sponge or fibrous porous material. Such material is compressible when dry, because air is easily expelled from the pores and/or interstices of material when compressed. The seal 74 may therefore adopt a compressed state without increasing the bulk of the stent-valve 10 significantly. Once implanted, blood may penetrate and fill the pores and/or interstices of the seal material. The blood may become trapped in the pores and/or interstices, thereby creating a barrier to blood flow through the material. The blood may also cause distension of the seal material to further expand the seal outwardly and fill any gaps of voids around the stent-valve 10.

Figure 9A:
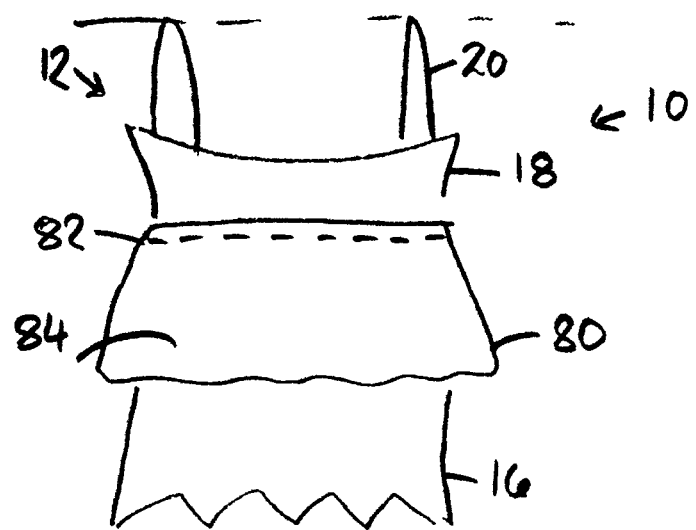
FIG. 9a is a schematic side view of a seal arrangement comprising a floating skirt.

FIG. 9 illustrates a seal in the form of a flexible skirt 80. The skirt 80 depends, for example, from the junction between the upper crown 18 and the lower portion 16 of the stent 16, to at least partly overlap the lower portion 16. A first (e.g. upper) portion 82 of the skirt 80 is coupled to the stent 12, to hold the skirt 80 captive. For example, the first portion 82 may be sutured to the stent 12. A second (e.g. depending) portion 84 of the skirt 80 is generally unconstrained, and is free to float relative to the stent 12.

Figure 9B:
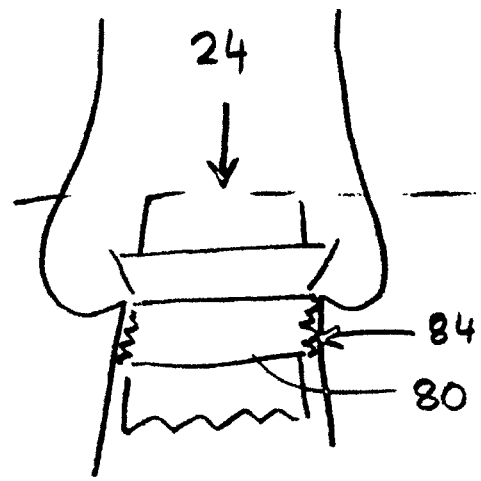
FIG. 9b is a schematic side view of the effect of the seal arrangement of FIG. 9a when implanted.

As illustrated in FIG. 9b (and explained above in relation to FIG. 1), the implantation procedure for the stent-valve 10 may involve displacing the stent-valve in the direction of arrow 24 to seat the upper crown 18 against native valve leaflets. The friction between the floating second portion 84 of the skirt 80, and the surrounding tissue/lumen may cause the second portion 84 to bunch or wrinkle axially, thus creating an excess of material that is able to seal any gap between the stent-valve 10 and the surrounding tissue/lumen.

Figure 10:
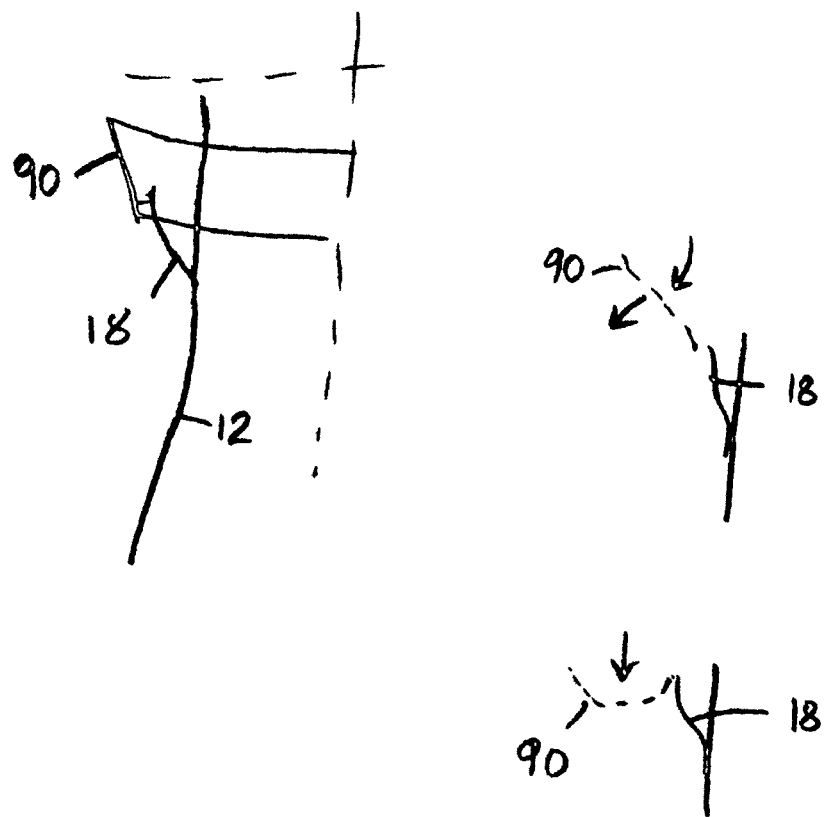
FIG. 10 is a schematic illustration of an alternative arrangement of a floating skirt seal.

FIG. 10 illustrates an alternative seal in the form of a flexible skirt 90. In contrast to the skirt of FIG. 9, the skirt 90 projects from the upper crown 18 towards the upper end of the stent 12. As indicated in phantom, under back pressure of blood, or reverse flow of blow around the stent-valve 10, the flexible skirt bears outwardly to seal against the surrounding tissue/lumen. The flexible skirt may form a channel shape section such that the back pressure of blood increases the sealing pressure against the surrounding tissue/lumen.

Figure 11:
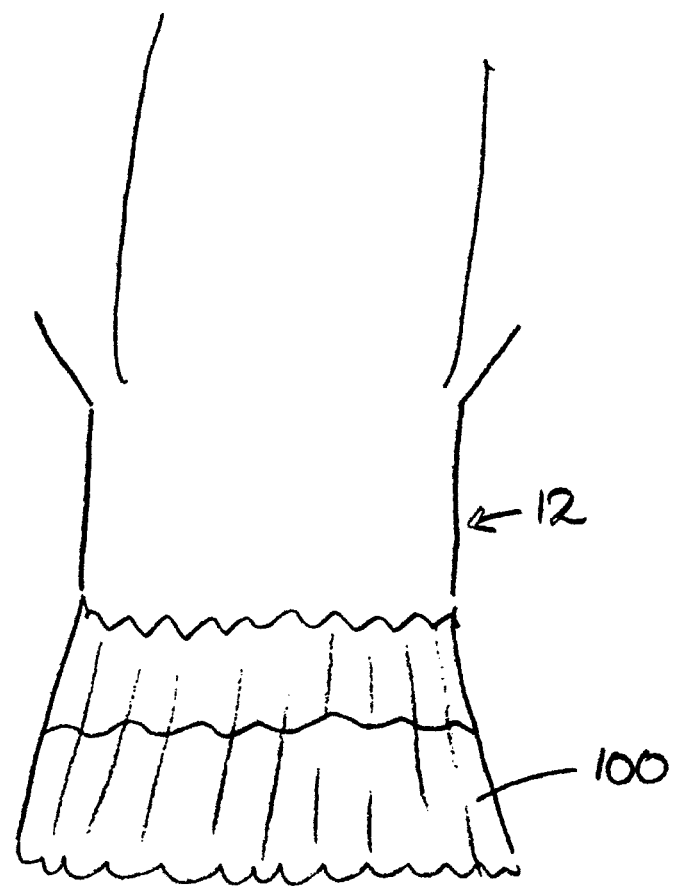
FIG. 11 is a schematic illustration of an alternative seal arrangement using a plated skirt.

FIG. 11 illustrates an alternative seal in the form of an oversized flexible skirt 100 that is connected to the stent 12 at one or more positions to define pleating or bunching. The connections may be by suturing. The pleating or bunching creates additional compliant material able to fill vids of gaps between the stent 12 and the surrounding tissue/lumen.

Figure 12:
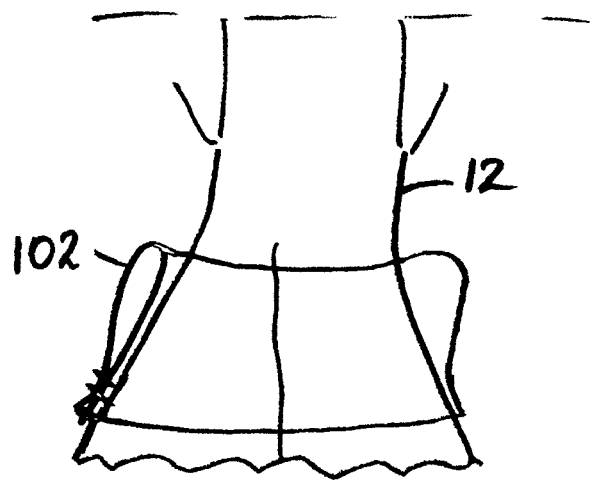
FIG. 12 is a schematic illustration of an alternative seal arrangement using a folded skirt.

FIG. 12 illustrates an alternative seal in the form of a skirt that is folded to define a cuff 102. The skirt material is flexible, but the fold creates a radiused bend providing a natural bulge. The bulge biases the seal material outwardly in order to fill voids or gaps between the stent 12 and the surrounding tissue/lumen.

Figure 13:
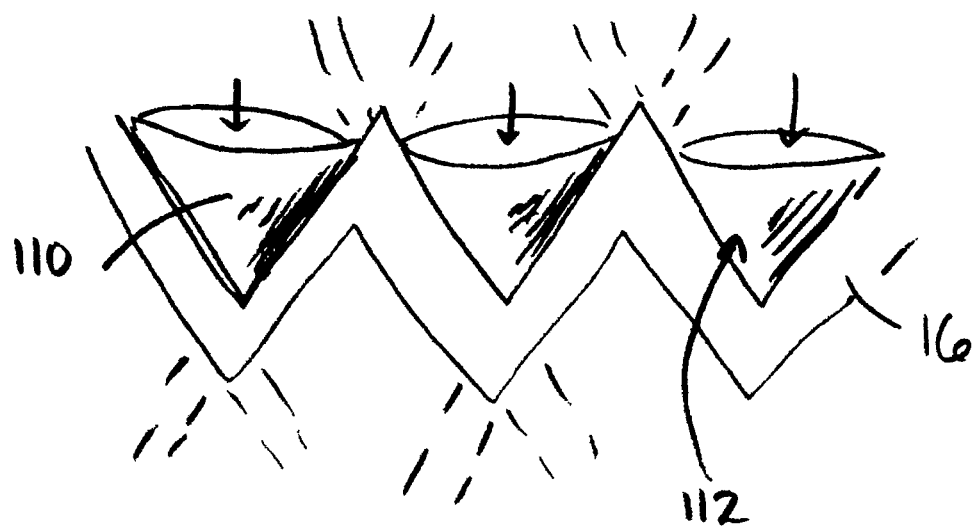
FIG. 13 is a schematic illustration of an alternative seal arrangement using distensible pockets.

FIG. 13 illustrates an alternative seal comprising a plurality of flexible pockets 110. Each pocket may be associated with a respective aperture 112 of a lattice structure of the stent, for example, the lower portion 16 and/or the upper crown 18. The pocket 110 may be defined by a flexible web of material. One wall of the pocket may be define by a portion of the outer skirt. Another wall of the pocket may be defined by a portion of the inner skirt. The pocket may be open on one side facing towards the outlet end of the stent, and closed in the opposite direction. In a stowed state, the pocket may collapse or fold substantially flat so as not to increase the bulk of the stent-valve. Once deployed, the pocket may open either under the influence of natural resilience, or under the influence of blood back pressure entering the mouth of the pocket. The back pressure causes the pocket to distend outwardly against surrounding tissue/lumen, and thereby further obstructing leakage of blood around the outside of the stent-valve 10.

Figure 14:
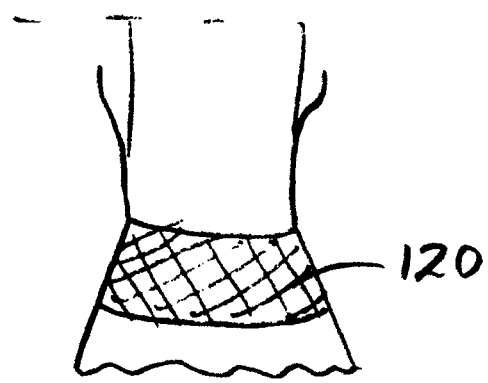
FIG. 14 is a schematic drawing of an alternative sealing arrangement using swellable material.

FIG. 14 illustrates an alternative seal arrangement comprising material 120 that swells in response to contact with blood. The swelling characteristics increase the bulk of the seal, enabling the seal to distend to fill any gaps between the stent-valve 10 and the surrounding tissue/lumen. Example swellable materials include a hydrogel and/or a liquid swellable polymer, and/or a so called superabsorbent material. The material may, for example, be carried by, or impregnated or otherwise embodied within the outer skirt. For example, the skirt may be of fabric comprising fibres of the swellable material. The material may be captive within a containing chamber, for example a flexible and/or distensible pouch or cuff. The combination of inner and outer skirts, with one comprising swellable material, can provide an especially effective seal arrangement. Further background information of use of, for example, a hydrogel for stent-valves may be found in US 2005/137688.

Figure 18:
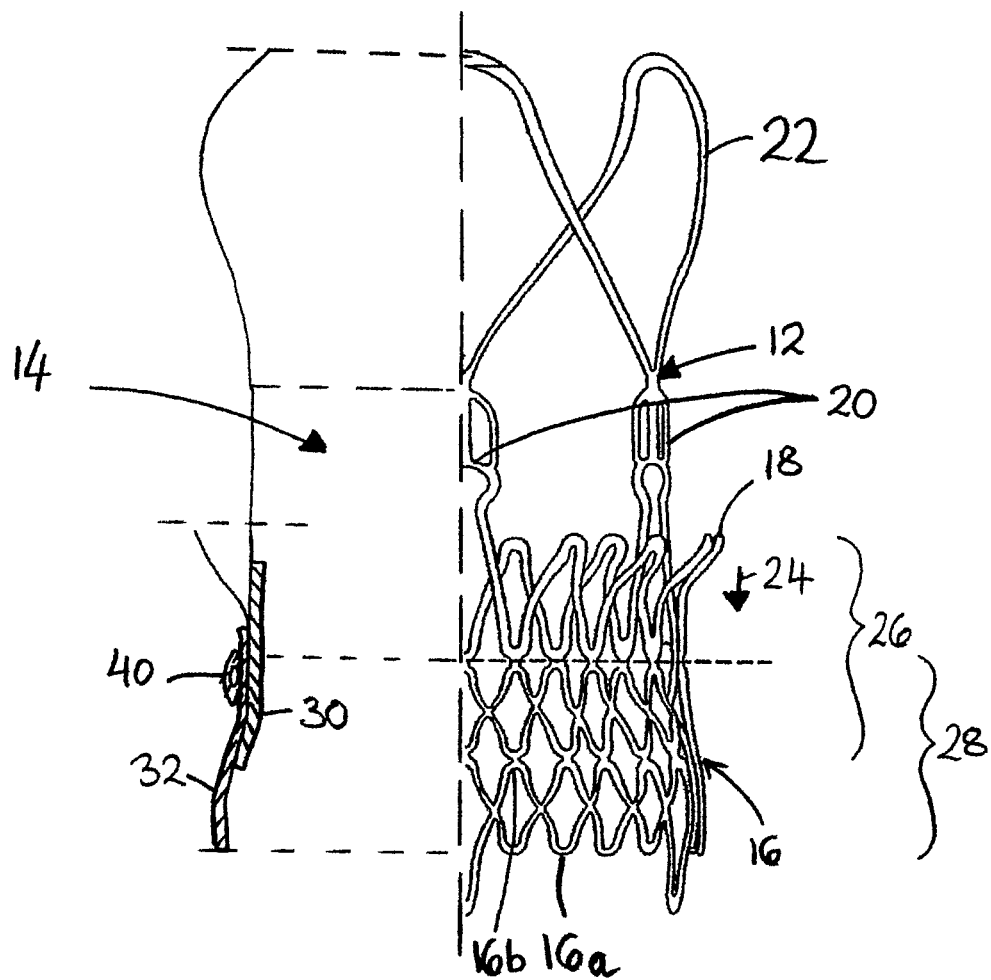
FIG. 18 is a partial schematic view of optional details of a stent-valve of FIG. 1.
Figure 19:
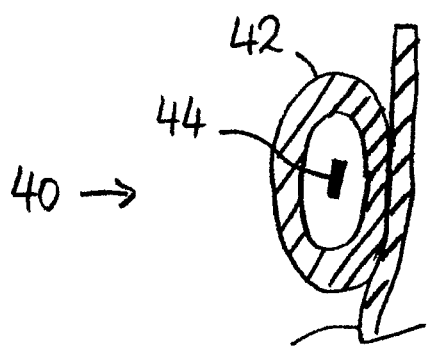
FIG. 19 is a schematic section of the paravalve seal of FIG. 18.
Figure 20:
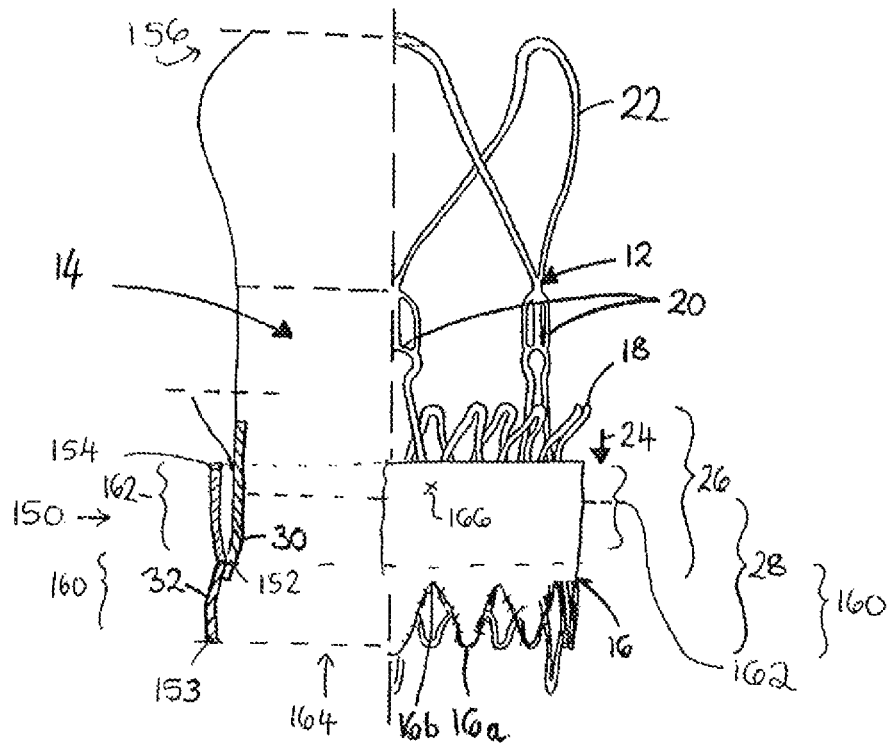
FIG. 20 is a partial schematic side view (with partial section to the left) of a further alternative sealing arrangement using a skirt defining an annular flap.

The seal of FIG. 14 is also illustrated in other embodiments of FIGS. 18 and 19. The swellable material is denoted by numeral 44, the containing chamber 42, together defining the paravalve seal 40 carried by, or comprised within, the outer skirt 32.

Figure 15:
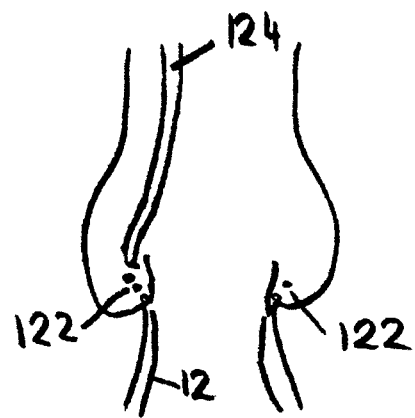
FIG. 15 is a schematic drawing illustrating administration of a sealant around the stent-valve.

FIG. 15 illustrates an alternative seal arrangement in which a sealant 122 is dispensed from the delivery catheter 124 (or from a further delivery catheter inserted after implantation), in order to seal around the periphery of the stent valve 10. For example, the sealant is dispensed on the outflow side of the stent-valve to seal any gaps between the upper crown and the native leaflets.

Figure 16:
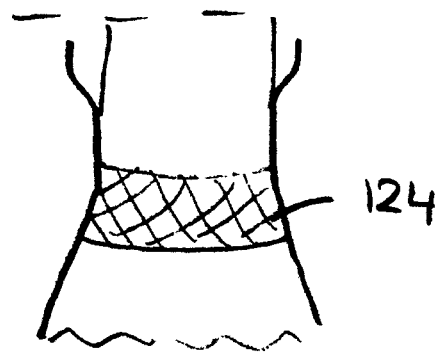
FIG. 16 is a schematic view of an alternative sealing arrangement using coagulation material.

FIG. 16 illustrates an alternative seal arrangement comprising material 124 that provides haemostatic and/or coagulant effects in response to contact with blood. The material 124 may, for example, be carried by, or impregnated or otherwise embodied within the outer skirt. The material may be captive within a containing chamber, for example a flexible and/or distensible pouch or cuff. The combination of inner and outer skirts, with one comprising such material, can provide an especially effective seal arrangement.

Figure 17:
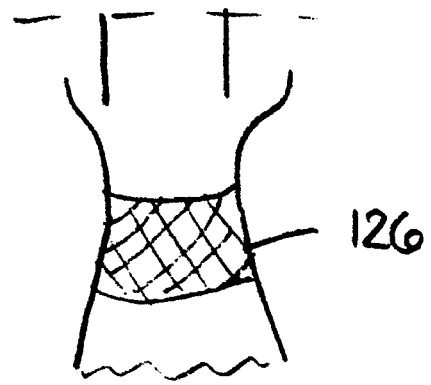
FIG. 17 is a schematic view of an alternative sealing arrangement using material that elutes calcium locally.

FIG. 17 illustrates an alternative seal arrangement comprising material 126 that elutes calcium locally. The calcium may deposit directly or indirectly against the surrounding tissue/lumen such that any gaps can be occluded. The material 126 may, for example, be carried by, or impregnated or otherwise embodied within the outer skirt. The material may be captive within a containing chamber, for example, a flexible and/or distensible pouch or cuff. The combination of inner and outer skirts, with one comprising such material, can provide an especially effective seal arrangement.

FIGS. 20-23 illustrate an alternative seal in the form of a flexible skirt 150. The skirt 150 may be the outer skirt 32 previously described. The skirt 150 may be attached to the stent 12 and/or inner skirt 30 at least at one or more attachment positions 152 spaced from an end 154 of the skirt 150 closest to the outlet end 156 of the stent-valve 10. The one or more attachment positions 152 may be such as to define a first skirt portion 160 captive with respect to the stent 12, and a second or further skirt portion 162 free to deploy or float relative to the stent 12. The one or more attachment positions 152 may, for example, correspond to an inlet end 164 of the stent-valve 10 and/or to an intermediate position between the extremities of the upper crown 18 and the lower portion 16. At least one attachment position 152 may overlap, at least partly, the inner skirt 30. Optionally, at least one attachment position 152 forms a direct attachment between the (e.g. outer) seal skirt 150 and the inner skirt 30. Such attachment can obstruct leakage of blood between the skirts 30 and 150.

As already explained with respect to FIG. 18, optionally, the lower portion 16 has an extremity formed with a substantially zig-zag shape. The zig-zag shape may comprise lower apexes 16a and upper apexes 16b. The upper apexes 16b may be masked in FIG. 20 by the superimposed presentation of both the frontmost and rearmost cells of the lattice structure. The zig-zag shape may be substantially continuous around the circumference of the stent 12. The (e.g. outer) seal skirt 150 may have a peripheral edge 153 having a zigzag shape that matches substantially the zig-zag shape of the extremity of the lower portion 16. Such an arrangement can avoid excessive material at the extremity, and thereby facilitate crimping of the stent-valve 10. At the same time, the (e.g. outer) seal skirt 150 covers (for example, completely) open cells of the lattice structure down to the stent extremity to reduce risk of blood leakage through the apertures of the cells. The (e.g. outer) seal skirt 150 can also provide a layer of material over the struts of the stent, thereby to cushion the engagement between the stent and the sensitive native heart tissue.

The second portion 162 of the skirt 150 may define a pocket or flap that is able to distend outwardly under backpressure or backflow of blood. The flap or pocket may extend continuously over an angle of at least about 180 degrees, optionally at least about 270 degrees, optionally about 360 (e.g. correspond to entirely around the circumferential periphery). The flap or pocket may be substantially annular and/or channel shaped.

In use, when the stent-valve is in its implanted position, the second portion 162 of the skirt may distend against surrounding tissue, for example, under backpressure of blood acting on the stent-valve 10 when the valve 14 has closed, or para-valve leakage of blood backflowing around the stent-valve 10. Distention of the second skirt portion 162 may define a pocket, such that the backpressure of blood within the pocket effects a seal against the surrounding tissue. In some aspects, the second skirt portion 162 may function similarly to the skirt 90 of FIG. 10, but positioned closer to the inlet end of the stent than in FIG. 10.

Figure 21:
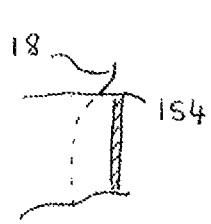
FIGS. 21-23 are partial schematic sections of a detail of FIG. 20, showing alternative heights of skirt with respect to the upper crown of the stent, in other embodiments.
Figure 22:
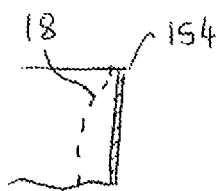
Figure 23:
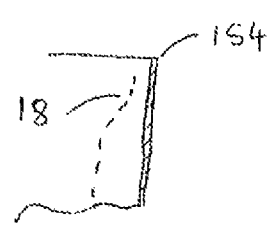

The skirt 150 may be dimensioned such that the end 154 closest to the outlet may be positioned axially at a desired position. For example, in FIG. 20, the end 154 may be positioned to be substantially at a waist of the stent 12 between the extremities of the upper crown 18 and the lower portion 16. In FIG. 21, the end 154 may be positioned part way up the upper crown 18 (e.g. intermediate the waist and the extremity of the upper crown 18). In FIG. 22, the end 154 may be positioned substantially in register with the extremity of the upper crown 18. In FIG. 23, the end 154 may be positioned beyond the extremity of the upper crown 18 (e.g. extending at least partly beyond the upper crown 18 towards the outlet end of the stent-valve 10).

At least in the examples of FIGS. 21-23, the upper crown 18 may act as a seal support. When the upper crown 18 is deployed, the upper crown 18 may at least partly bias the second skirt portion 162 outwardly, for example with respect to the waist between the upper crown 18 and the lower portion 16. Such biasing may urge the second skirt portion 162 (i) into engagement with surrounding tissue and/or (ii) to a distended shape defining a flap or pocket responsive to blood back-pressure and/or blood back-flow around the exterior of the stent-valve 10. The upper crown 18 (and seal support) may comprise cantilever elements. The cantilever elements may be flexible independently of one another. Each cantilever element may have a U-shape or V-shape. Each cantilever element may comprise a pair of struts that meet at the apex of the cantilever element.

In all examples, the end 154 may have a substantially straight edge, or it may have a non-straight edge, for example, an undulating shape, or castellated shape, or notched shape. The variations in a non-straight edge may optionally align with apexes of the upper crown 18. Providing a non-straight edge may, in some embodiments, enable a reduction in the bulk of material of the skirt 150 to be compressed for loading on to or in to a delivery apparatus, which may be significant when the skirt 150 overlaps a region of the stent-valve 10 that is "crowded" in terms of stent material and/or leaflet material and/or skirt material to be compressed.

In some embodiments, the second skirt portion 162 may be wholly unattached to the stent 12. Alternatively, in some embodiments, one or more control attachments 166 may be formed between the second skirt portion 162 and the stent 12 (for example, the upper crown 18). The control attachments 166 may be configured to permit the second skirt portion 162 to distend substantially freely, while preventing unwanted everting of the second skirt portion 162 (e.g. during compression and loading the stent-valve by an inexperienced user).

Figure 24:
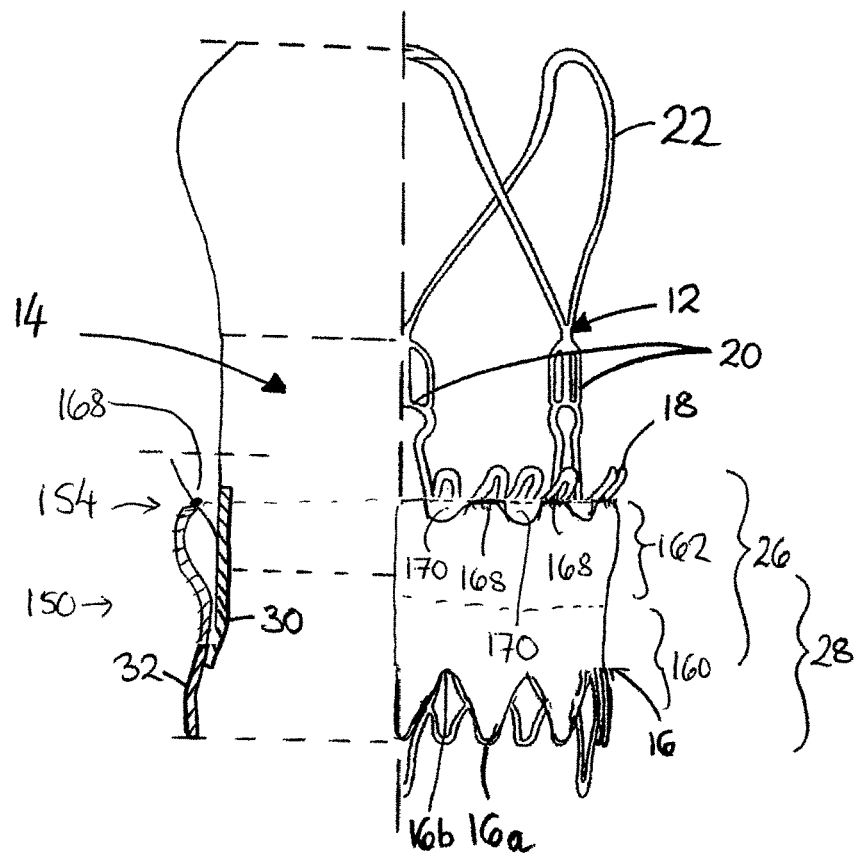
FIG. 24 is a partial schematic side view (with partial section to the left) of a further alternative sealing arrangement using a skirt defining an annular pocket.
Figure 25:
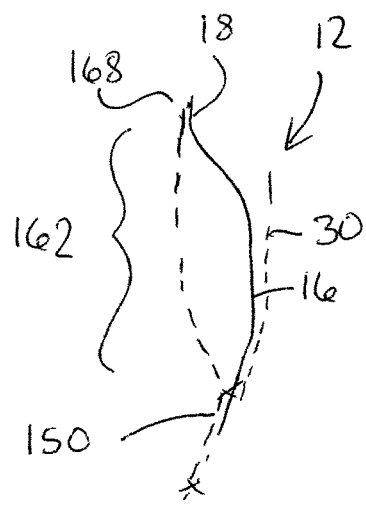
FIG. 25 is a partial schematic section showing a detail of FIG. 24, with an alternative height of skirt with respect to the upper crown of the stent, in an alternative embodiment.
Figure 26:
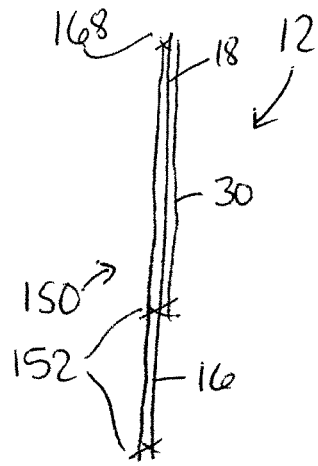
FIG. 26 is a partial schematic view of the arrangement of FIG. 25 in a compressed condition for loading into a delivery apparatus for implantation.

FIGS. 24-26 illustrate a further modification of the seal arrangement of FIGS. 20-23. In FIGS. 24-26, the end 154 of the seal is attached to the upper crown 18 at plural positions 168 around the circumferential edges of the end 154, to define an annular pocket or annular channel shape of the second skirt portion 162. In use, the second skirt portion 162 may distend or billow outwardly from the stent, as a distensible cuff, in response to backpressure and/or backflow of blood. The second skirt portion 162 may optionally have a clearance, and/or an aperture and/or a notch between adjacent positions 170, to define a communication port to allow blood to enter the annular pocket. For example, the end 154 may have a castellated and/or notched and/or scalloped and/or undulating edge to define such communication ports.

The upper crown 18 may act as a seal support. For example, the attachment positions 168 may directly support the second skirt portion 162. Additionally or alternatively, when the upper crown 18 is deployed, the upper crown 18 may at least partly bias the second skirt portion 162 outwardly, for example with respect to the waist between the upper crown 18 and the lower portion 16. Such biasing may urge the second skirt portion 162 (i) into engagement with surrounding tissue and/or (ii) to a distended shape defining a flap or pocket responsive to blood back-pressure and/or blood back-flow around the exterior of the stent-valve 10. The upper crown 18 (and seal support) may comprise cantilever elements. The cantilever elements may be flexible independently of one another. Each cantilever element may have a U-shape or V-shape. Each cantilever element may comprise a pair of struts that meet at the apex of the cantilever element.

Attachment of the end 154 to the upper crown may provide additional control over the otherwise free second skirt portion 162. Such an arrangement may facilitate, for example, compressing and loading of the stent-valve 10 for implantation, and avoid risk of the second skirt portion 162 being accidentally everted.

The attachment positions 168 between the end 154 of the skirt 150 and the upper crown 18 may be chosen and/or varied as desired. In the embodiment of FIG. 25, the attachment positions 168 may correspond to the extremity of the upper crown 18. In FIG. 24, the attachment positions 168 may correspond to an intermediate position partway up the upper crown 18 (for example, intermediate the extremity of the upper crown 18, and the waist between the upper crown 18 and lower portion 16).

FIG. 26 illustrates how the upper crown 18, and the skirt 150 of FIG. 25, may be compressed to a stowed configuration when the stent-valve 10 is compressed using a loading apparatus (for example, a crimper or a compression funnel) for loading the stent-valve into or on to a delivery device (for example a delivery catheter, not shown). The upper crown 18 and the second skirt portion 162 may lie substantially flat with the remainder of the stent 12. Upon deployment, the upper crown 18 and the second skirt portion 162 may deploy radially outwardly (to the shape shown in FIG. 25).

The skirt 150 may have any desired profile shape. For example, in some embodiments, the skirt 150 may have a substantially cylindrical shape. The diameter of the cylindrical shape may correspond to the maximum diameter of the lower portion 16 and/or to the diameter of the stent 12 (e.g. upper crown 18) at the point reached by the end 154 of the skirt 150, and/or the maximum diameter of the upper crown 18, and/or a dimension larger than the upper crown. The waist defined between the upper crown 18 and the lower portion 16, and/or the oversizing of a stent 12 with respect to the size of the native valve to be replaced (typically about 1, 2 or 3 mm diameter oversizing), may provide an excess of skirt material able to distend or billow outwardly for the sealing effect. Additionally or alternatively, the skirt 150 may be sculpted with a non-cylindrical shape, for example, a bulbous shape or a funnel shape, also to provide excess material able to distend or billow outwardly for the sealing effect.

As already described, the seals and/or skirts of any of the forgoing embodiments may be made of any suitable material. Suitable material may include biological tissue (for example, pericardium (for example, porcine pericardium or bovine pericardium). Additionally or alternatively, suitable material may include plastics (for example, PET or PEEK). Plastics may be used in woven or non-woven fabric form, and/or in sheet form, and/or in film form.

Although the seal arrangements have been described as alternatives, it is envisaged that any two or more of the seal arrangements may be combined for synergistic effect. It will also be appreciated that the foregoing description is merely illustrative of example forms of the invention and that many modifications and alternatives may be used within the scope of the invention.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the presented disclosure and their equivalents. Moreover, embodiments of the subject disclosure may include methods, systems and devices which may further include any and all elements from any other disclosed methods, systems and devices including any and all elements corresponding to stent-valves and/or seals for stent-valves. In other words, elements from one or another disclosed embodiments may be interchangeable with elements from other disclosed embodiments. In addition, one or more features of disclosed embodiments may be removed and still result in patentable subject matter (and this, resulting in yet more embodiments of the subject disclosure).

The invention claimed is:

1. A stent-valve for transcatheter implantation to replace a cardiac valve, the stent valve being compressible to a compressed state for delivery, and expandable to an operative state for implantation, the stent-valve comprising:
a stent,
a plurality of leaflets for defining a prosthetic valve, and
a paravalve seal for sealing against surrounding tissue, wherein the seal comprises a skirt, at least a first portion of which is captive with respect to the stent, and at least a second portion of which is free to deploy or float relative to the stent,
wherein the skirt is an outer skirt carried on an exterior of the stent, and wherein the stent-valve has an inlet end and an outlet end, wherein:
the stent-valve further comprises an inner skirt communicating with the leaflets and carried on an interior of the stent,
wherein:
the outer skirt is attached directly to the inner skirt at one or more attachment positions, said attachment positions spaced from an end of the outer skirt closest to the outlet end of the stent-valve, to obstruct leakage of blood between the inner skirt and outer skirt,
the first portion of the outer skirt extends outside the stent from the one or more attachment positions towards the inlet end of the stent-valve; and
the second portion of the outer skirt extends from the one or more attachment positions, outside the stent towards the outlet end of the stent-valve, whereby in use the second portion can distend outwardly to seal against surrounding tissue under backpressure or back-flow of blood.

2. The stent-valve of claim 1, wherein the second portion of the outer skirt forms a wall of a pocket, the pocket being open towards the outlet end of the stent-valve.

3. The stent-valve of claim 1, wherein the inner skirt extends further than the outer skirt towards the outlet end of the stent-valve.

4. The stent-valve of claim 1, wherein the outer skirt extends further than the inner skirt towards the inlet end of the stent-valve.

5. The stent-valve of claim 4, wherein the inner skirt extends further than the outer skirt towards the outlet end of the stent-valve.

6. The stent-valve of claim 1, further comprising one or more control attachments between the second skirt portion and the stent.

7. The stent-valve of claim 1, wherein the stent comprises:
a lower tubular portion;
an upper crown communicating with the lower tubular portion;
a plurality of upstanding commissural supports communicating with the lower tubular portion and upstanding relative to the upper crown portion; and
a plurality of stabilization arches communicating with the commissural supports.

8. A stent-valve for transcatheter implantation to replace a cardiac valve, the stent valve being compressible to a compressed state for delivery, and expandable to an operative state for implantation, the stent-valve comprising:
a stent,
a plurality of leaflets for defining a prosthetic valve, and
a paravalve seal for sealing against surrounding tissue,
wherein the seal comprises a skirt, at least a first portion of which is captive with respect to the stent, and at least a second portion of which is free to deploy or float relative to the stent,
wherein the skirt is an outer skirt carried on an exterior of the stent, and wherein the stent-valve has an inlet end and an outlet end, wherein:
the stent-valve further comprises an inner skirt communicating with the leaflets and carried on an interior of the stent,
wherein:
the outer skirt is attached directly to the inner skirt at one or more attachment positions, said attachment positions spaced from an end of the outer skirt closest to the outlet end of the stent-valve, to obstruct leakage of blood between the inner skirt and outer skirt,
the first portion of the outer skirt extends from the one or more attachment positions towards the inlet end of the stent-valve; and
the second portion of the outer skirt extends from the one or more attachment positions to the end of the outer skirt closest to the outlet end of the stent-valve, defining a wall of a pocket open towards the outlet end of the stent valve, whereby in use the second portion can distend outwardly to seal against surrounding tissue under back-pressure or back-flow of blood.

9. The stent-valve of claim 8, wherein the inner skirt extends further than the outer skirt towards the outlet end of the stent-valve.

10. The stent-valve of claim 8, wherein the outer skirt extends further than the inner skirt towards the inlet end of the stent-valve.

11. The stent-valve of claim 10, wherein the inner skirt extends further than the outer skirt towards the outlet end of the stent-valve.

12. The stent-valve of claim 8, further comprising one or more control attachments between the second skirt portion and the stent.

13. The stent-valve of claim 8, wherein the stent comprises:
a lower tubular portion;
an upper crown communicating with the lower tubular portion;
a plurality of upstanding commissural supports communicating with the lower tubular portion and upstanding relative to the upper crown portion; and
a plurality of stabilization arches communicating with the commissural supports.

14. A stent-valve for transcatheter implantation to replace a cardiac valve, the stent valve being compressible to a compressed state for delivery, and expandable to an operative state for implantation, the stent-valve comprising:
a stent,
a plurality of leaflets for defining a prosthetic valve, and
a paravalve seal for sealing against surrounding tissue,
wherein the seal comprises a skirt, at least a first portion of which is captive with respect to the stent, and at least a second portion of which is free to deploy or float relative to the stent,
wherein the skirt is an outer skirt carried on an exterior of the stent, and wherein the stent-valve has an inlet end and an outlet end, wherein:
the stent-valve further comprises an inner skirt communicating with the leaflets and carried on an interior of the stent, the inner skirt extending further than the outer skirt towards the outlet end of the stent valve,
wherein:
the outer skirt is attached directly to the inner skirt at one or more attachment positions, said attachment positions spaced from an end of the outer skirt closest to the outlet end of the stent-valve, to obstruct leakage of blood between the inner skirt and outer skirt, the first portion of the outer skirt extends from the one or more attachment positions towards the inlet end of the stent-valve; and the second portion of the outer skirt extends from the one or more attachment positions to the end of the outer skirt closest to the outlet end of the stent-valve, whereby in use the second portion can distend outwardly to seal against surrounding tissue under back-pressure or back-flow of blood.

15. The stent-valve of claim 14, wherein the outer skirt extends further than the inner skirt towards the inlet end of the stent-valve.

16. The stent-valve of claim 14, further comprising one or more control attachments between the second skirt portion and the stent.

17. The stent-valve of claim 14, wherein the stent comprises:
a lower tubular portion;
an upper crown communicating with the lower tubular portion;
a plurality of upstanding commissural supports communicating with the lower tubular portion and upstanding relative to the upper crown portion; and
a plurality of stabilization arches communicating with the commissural supports.

18. A stent-valve for transcatheter implantation to replace a cardiac valve, the stent valve being compressible to a compressed state for delivery, and expandable to an operative state for implantation, the stent-valve comprising:
a stent,
a plurality of leaflets for defining a prosthetic valve, and
a paravalve seal for sealing against surrounding tissue,
wherein the seal comprises a skirt, at least a first portion of which is captive with respect to the stent, and at least a second portion of which is free to deploy or float relative to the stent,
wherein the skirt is an outer skirt carried on an exterior of the stent, and wherein the stent-valve has an inlet end and an outlet end, wherein:
the stent-valve further comprises an inner skirt communicating with the leaflets and carried on an interior of the stent,
wherein:
the outer skirt extends further than the inner skirt towards the inlet end of the stent-valve, and is attached directly to the inner skirt at one or more attachment positions, said attachment positions spaced from an end of the outer skirt closest to the outlet end of the stent-valve, to obstruct leakage of blood between the inner skirt and outer skirt,
the first portion of the outer skirt extends from the one or more attachment positions towards the inlet end of the stent-valve; and
the second portion of the outer skirt extends from the one or more attachment positions to the end of the outer skirt closest to the outlet end of the stent-valve, whereby in use the second portion can distend outwardly to seal against surrounding tissue under back-pressure or back-flow of blood.

19. The stent-valve of claim 18, further comprising one or more control attachments between the second skirt portion and the stent.

20. The stent-valve of claim 18, wherein the stent comprises:
a lower tubular portion;
an upper crown communicating with the lower tubular portion;
a plurality of upstanding commissural supports communicating with the lower tubular portion and upstanding relative to the upper crown portion; and
a plurality of stabilization arches communicating with the commissural supports.

* * * * *